United States Patent
Tada et al.

(10) Patent No.: US 7,906,668 B2
(45) Date of Patent: Mar. 15, 2011

(54) IMIDE COMPLEX, METHOD FOR PRODUCING THE SAME, METAL-CONTAINING THIN FILM AND METHOD FOR PRODUCING THE SAME

(75) Inventors: Ken-ichi Tada, Fujisawa (JP); Taishi Furukawa, Ayase (JP); Koichiro Inaba, Shunan (JP); Tadahiro Yotsuya, Sagamihara (JP); Hirokazu Chiba, Machida (JP); Toshiki Yamamoto, Machida (JP); Tetsu Yamakawa, Nishitokyo (JP); Noriaki Oshima, Yokohama (JP)

(73) Assignees: Tosoh Corporation, Shunan-shi (JP); Sagami Chemical Research Center, Ayase-shi (JP)

( * ) Notice: Subject to any disclaimer, the term of this patent is extended or adjusted under 35 U.S.C. 154(b) by 191 days.

(21) Appl. No.: 12/439,364

(22) PCT Filed: Aug. 20, 2007

(86) PCT No.: PCT/JP2007/066135
§ 371 (c)(1),
(2), (4) Date: Feb. 27, 2009

(87) PCT Pub. No.: WO2008/026470
PCT Pub. Date: Mar. 6, 2008

(65) Prior Publication Data
US 2010/0010248 A1    Jan. 14, 2010

(30) Foreign Application Priority Data

| Aug. 28, 2006 | (JP) | 2006-231081 |
| Mar. 26, 2007 | (JP) | 2007-079924 |
| Jul. 17, 2007 | (JP) | 2007-186071 |

(51) Int. Cl.
*C07F 9/00* (2006.01)
*C23C 16/00* (2006.01)

(52) U.S. Cl. .......... 556/42; 427/248.1; 427/250
(58) Field of Classification Search .......... 556/42; 427/248.1, 250
See application file for complete search history.

(56) References Cited

FOREIGN PATENT DOCUMENTS

| JP | 2003-335740 A | 11/2003 |
| JP | 2006-131606 A | 5/2006 |
| WO | 2006049059 A1 | 5/2006 |

OTHER PUBLICATIONS

Hsin-Tien Chiu et al., Syntheses and Characterization of Organoimido Complexes of Niobium(V); Potential CVD Precursors, Journal of the Chinese Chemical Society, 1998, pp. 355-360, vol. 45, No. 3.

Kaupo Kukli et al., Atomic Layer Deposition and Chemical Vapor Deposition of Tantalum Oxide by Successive and Simultaneous Pulsing of Tantalum Ethoxide and Tantalum Chloride, Chemistry of Materials, 2000, pp. 1914-1920, vol. 12 No. 7, American Chemical Society.

William A. Nugent et al., Electrophilic vs. Nucleophilic Reactivity in Complexes Containing Multiply-Bonded (Alkylidene, Imido or Oxo) Ligands. A Conceptual Model, Inorganica Chimica Acta 65, 1982, pp. L91-L93.

*Primary Examiner* — Porfirio Nazario Gonzalez
(74) *Attorney, Agent, or Firm* — Sughrue Mion, PLLC

(57) ABSTRACT

Objects of the present invention are to provide a novel niobium or tantalum complex having good vapor pressure and becoming a raw material for producing a niobium- or tantalum-containing thin film by a method such as CVD method, ALD method or the like, a method for producing the same, a metal-containing thin film using the same, and a method for producing the same. The present invention relates to producing an imide complex represented by the general formula (1) by, for example, the reaction between $M^1(NR^1)X_3(L)_r$ (2) and an alkali metal alkoxide (3):

[Chem. 1]

$$M^1(NR^1)X_3(L)_r + R^2OM^2 \longrightarrow M^1(NR^1)(OR^2)_3$$
$$(2) \qquad\qquad (3) \qquad\qquad (1)$$

(wherein $M^1$ represents niobium atom or tantalum atom, $R^1$ represents an alkyl group having from 1 to 12 carbon atoms, $R^2$ represents an alkyl group having from 2 to 13 carbon atoms, X represents halogen atom, r is 1 when L is 1,2-dimethoxyethane ligand, r is 2 when L is pyridine ligand, and $M^2$ represents an alkali metal), and producing a niobium- or tantalum-containing thin film by using the imide complex (1) as a raw material.

14 Claims, 10 Drawing Sheets

IMIDE COMPLEX, METHOD FOR PRODUCING THE SAME, METAL-CONTAINING THIN FILM AND METHOD FOR PRODUCING THE SAME

TECHNICAL FIELD

The present invention relates to a metal complex useful in the production of a semiconductor device, a method for producing the same, a metal-containing thin film, and a method for producing the same.

BACKGROUND ART

Silicon oxynitride (SiON) and alumina ($Al_2O_3$) have been used as main materials in DRAM capacitor dielectric of semiconductor devices hitherto developed. However, in the next generation of semiconductors, reduction in size in devices is required to meet high performance, and a material having further high dielectric constant is required as a material of the next generation of capacitor dielectric. At present, tantalum oxide and niobium oxide are noted as a novel material used in capacitor dielectric.

A method for forming a thin film presently used as a semiconductor device includes physical vapor deposition method (PVD method) by sputtering and chemical vapor deposition method (CVD method). However, the next generation or more of semiconductor production requires to form a uniform and thin film on the surface of a complicated three-dimensional structure of a device having reduced size. Accordingly, PVD method which is difficult to form a uniform film on a patterned indented surface is not appropriate. For this reason, a method for forming a thin film by CVD method of sending a raw material as a gas to a reaction chamber and decomposing the same to deposit a film or an atomic layer deposition method (ALD method) of decomposing a raw material adsorbed on a substrate surface to deposit a film is investigated as a method for preparing a thin film with good step coverage.

In the production of a semiconductor device, a material having appropriate vapor pressure and thermal stability and capable of vaporizing in a stable supply amount is selected as a material for forming a thin film by CVD method or ALD method. Furthermore, it is one of necessary requirements that a film having uniform thickness can be formed on the surface of a complicated three-dimensional structure. Furthermore, it is preferred that a material is liquid at the time of supplying.

Use of amide compounds (for example, Patent Document 1 and Non-Patent Document 1) and pentaalkoxides (for example, Non-Patent Document 2) is investigated as a material for forming a niobium oxide thin film and a tantalum oxide thin film by CVD method or ALD method. However, of the amide compounds, $Nb(N^tPe)(NMe_2)_3$ is solid at room temperature, and $Nb(N^tBu)(NEt_2)_3$ and $Ta(N^tBu)(NEt_2)_3$ are liquid at room temperature, but have low vapor pressure. Pentaalkoxides such as $Nb(OEt)_5$ and $Ta(OEt)_5$ are liquid at room temperature, but have low vapor pressure. That is, those compounds have the respective problems on the use as a raw material for forming a thin film by CVD method or ALD method, and it is difficult to say that those compounds are most appropriate materials.

Patent Document 1: JP-A-2006-131606
Non-Patent Document 1: Journal of Chinese Chemical Society, vol. 45, p. 355 (1998)
Non-Patent Document 2: Chemistry of Materials, vol. 12, p. 1914 (2000)

DISCLOSURE OF THE INVENTION

Problems that the Invention is to Solve

Objects of the present invention are to provide a novel compound having good vapor pressure and becoming a raw material for producing a metal-containing thin film by a method such as CVD method, A/D method or the like, a method for producing the same, a metal-containing thin film using the same, and a method for producing the same.

Means for Solving the Problems

As a result of keen investigations in view of the above current situation, the present inventors have found that the above problems can be solved by an imide complex represented by the general formula (1), a method for producing the same, a metal-containing thin film using the imide complex (1) as a raw material, and a method for producing the same, and have reached to complete the present invention.

That is, the invention relates to an imide complex represented by the general formula (1):

[Chem. 1]

$$M^1(NR^1)(OR^2)_3 \quad (1)$$

(wherein $M^1$ represents niobium atom or tantalum atom, $R^1$ represents an alkyl group having from 1 to 12 carbon atoms, and $R^2$ represents an alkyl group having from 2 to 13 carbon atoms).

The invention further relates to a method for producing an imide complex represented by the general formula (1), which comprises reacting a compound represented by the general formula (2):

[Chem. 2]

$$M^1(NR^1)X_3(L)_r \quad (2)$$

(wherein $M^1$ and $R^1$ are the same as defined above, X represents halogen atom, L represents 1,2-dimethoxyethane ligand or pyridine ligand, r is 1 when L is 1,2-dimethoxyethane ligand, and r is 2 when L is pyridine ligand), and an alkali metal alkoxide represented by the general formula (3):

[Chem. 3]

$$R^2OM^2 \quad (3)$$

(wherein $R^2$ is the same as defined above, and $M^2$ represents an alkali metal).

The invention further relates to a method for producing an imide complex represented by the general formula (1), which comprises reacting a compound represented by the general formula (4):

[Chem. 4]

$$M^1(NR^1)(NR^3R^4)_3 \quad (4)$$

(wherein $M^1$ and $R^1$ are the same as defined above, and $R^3$ and $R^4$ each independently represent methyl group or ethyl group), and an alcohol represented by the general formula (5):

[Chem. 5]

$$R^2OH \quad (5)$$

(wherein $R^2$ is the same as defined above).

The invention further relates to a method for producing an imide complex represented by the general formula (1), which comprises reacting a compound represented by the general formula (1a):

[Chem. 6]

$$M^1(NR^{1a})(OR^2)_3 \quad (1a)$$

(wherein $M^1$ and $R^2$ are the same as defined above, and $R^{1a}$ represents tert-butyl group or isopropyl group), and an amine represented by the general formula (7):

[Chem. 7]

$$R^1NH_2 \quad (7)$$

(wherein $R^1$ is the same as defined above, provided that $R^1$ and $R^{1a}$ are not simultaneously the same group).

The invention further relates to a method for producing an imide complex represented by the general formula (1), which comprises reacting a metal halide represented by the general formula (8):

[Chem. 8]

$$M^1Y_5 \quad (8)$$

(wherein $M^1$ represents niobium atom or a tantalum atom, and Y represents halogen atom),
the alkali metal alkoxide represented by the general formula (3), and
lithium amide represented by the general formula (9):

[Chem. 9]

$$R^1NHLi \quad (9)$$

(wherein $R^1$ represents an alkyl group having from 1 to 12 carbon atoms).

The invention further relates to a method for producing a niobium- or tantalum-containing thin film, which comprises using the imide complex represented by the general formula (1) as a raw material.

The invention further relates to a niobium- or tantalum-containing thin film produced by the above production method.

ADVANTAGE OF THE INVENTION

The imide complex (1) of the present invention has good vapor pressure, and using this as a raw material, a niobium- or tantalum-containing thin film can be produced by a method such as CVD method, ALD method or the like.

DESCRIPTION OF REFERENCE NUMERALS AND SIGNS

Figure 1:
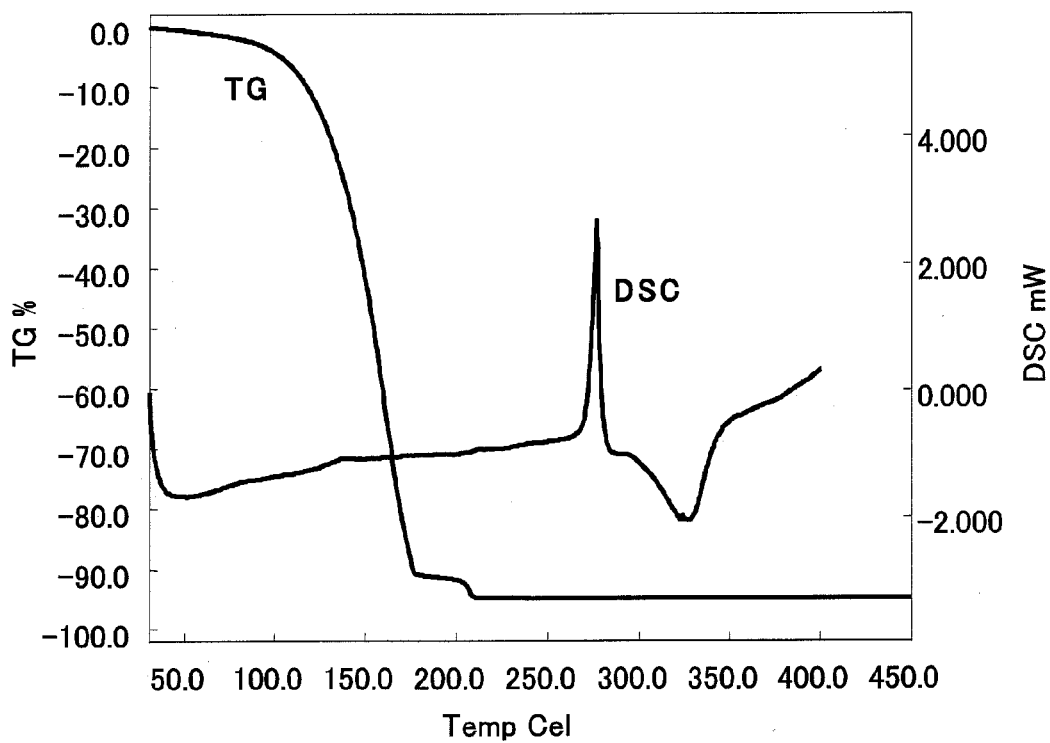
FIG. 1 is a view showing the results of TG and DSC measured in Example 1.

1. Raw material container
2. Thermostatic bath
3. Reaction chamber
4. Substrate
5. Reaction gas
6. Diluent gas
7. Carrier gas
8. Mass flow controller
9. Mass flow controller
10. Mass flow controller
11. Vacuum pump
12. Exhaust

BEST MODE FOR CARRYING OUT THE INVENTION

The present invention is described in more detail below.
Examples of the alkyl group having from 1 to 12 carbon atoms represented by $R^1$ include methyl group, ethyl group, propyl group, isopropyl group, butyl group, isobutyl group, sec-butyl group, tert-butyl group, pentyl group, isopentyl group, neopentyl group, tert-pentyl group, 1-methylbutyl group, 2-methylbutyl group, 1,2-dimethylpropyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, cyclopropyl group, cyclobutyl group, cyclopentyl group, cyclohexyl group, cyclopropyl-methyl group, cyclopropylethyl group, cyclobutylmethyl group, heptyl group, cyclohexylmethyl group, 1,1-diethyl-propyl group, 2-methylcyclohexyl group, 4-methylcyclohexyl group, octyl group, 2,5-dimethylcyclohexyl group, 3,5-dimethylcyclohexyl group, 1,1,3,3-tetramethylbutyl group, 1,1,2,3,3-pentamethylbutyl group, 1,1-diethyl-3,3-dimethylbutyl group, adamantyl group, 1,1-dimethyloctyl group, 1,1-dipropylbutyl group, 1,1-dimethyldecyl group, and 1,1-diethyloctyl group.

Examples of the alkyl group having from 2 to 13 carbon atoms represented by $R^2$ include ethyl group, propyl group, isopropyl group, butyl group, isobutyl group, sec-butyl group, tert-butyl group, pentyl group, isopentyl group, neopentyl group, tert-pentyl group, 1-methylbutyl group, 2-methylbutyl group, 1,2-dimethylpropyl group, hexyl group, isohexyl group, 1-methylpentyl group, 2-methylpentyl group, 3-methylpentyl group, 1,1-dimethylbutyl group, 1,2-dimethylbutyl group, 2,2-dimethylbutyl group, 1,3-dimethylbutyl group, 2,3-dimethylbutyl group, 3,3-dimethylbutyl group, 1-ethylbutyl group, 2-ethylbutyl group, 1,1,2-trimethylpropyl group, 1,2,2-trimethylpropyl group, 1-ethyl-1-methylpropyl group, 1-ethyl-2-methylpropyl group, cyclopropyl group, cyclobutyl group, cyclopentyl group, cyclohexyl group, cyclopropylmethyl group, cyclopropylethyl group, cyclobutylmethyl group, 1,1-dimethylpropyl group, 1-ethyl-1-methylpropyl group, 1,1-diethylpropyl group, 1-methyl-1-propylbutyl group, octyl group, 2,5-dimethylcyclohexyl group, 3,5-dimethylcyclohexyl group, 1,1,3,3-tetramethylbutyl group, 1,1,2,3,3-pentamethylbutyl group, 1,1-diethyl-3,3-dimethylbutyl group, adamantyl group, 1,1-dimethyloctyl group, 1,1-dipropylbutyl group, 1,1-dimethyldecyl group, 1,1-diethyloctyl group, 1,1-dimethylundecyl group, and 1,1-dibutylpentyl group.

In the point that the imide complex (1) has good vapor pressure, $R^1$ is preferably an alkyl group having from 1 to 10 carbon atoms, and $R^2$ is preferably an alkyl group having from 2 to 10 carbon atoms, and particularly preferably isopropyl group or tert-butyl group. Particularly, in the case that $M^1$ is niobium atom, $R^1$ is further preferably propyl group, isopropyl group or tert-butyl group, and $R^2$ is further preferably tert-butyl group. In the case that $M^1$ is tantalum atom, $R^1$ is further preferably isopropyl group or tert-butyl group, and $R^2$ is further preferably tert-butyl group.

The production method of the invention is described in detail below. Production method 1 is a method for producing the imide complex (1) of the invention by the reaction between the compound (2) and the alkali metal alkoxide (3).

[Chem. 10]

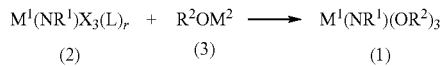

(wherein $M^1$, $R^1$, X, L, r, $R^2$ and $M^2$ are the same as defined above).

The production method 1 can be carried out in an organic solvent. Examples of the organic solvent include hydrocarbons such as pentane, hexane, heptane, octane, benzene, toluene, ethylbenzene and xylene; and ethers such as diethyl ether, diisopropyl ether, 1,2-dimethoxyethane, dioxane, tetrahydrofuran and cyclopentyl methyl ether. Those can be used alone or as mixtures thereof. It is preferred in the point of good yield to use tetrahydrofuran, hexane, toluene or a mixture of hexane and toluene.

In the production method 1, the reaction temperature is not limited. However, when the reaction is conducted at a temperature appropriately selected from a range of from –80 to 150° C., the imide complex (1) can be obtained in good yield. The reaction time is not limited. However, when the reaction is conducted in reaction time appropriately selected from a range of from 1 to 150 hours, the imide complex (1) can be obtained in good yield. It is further preferred in the point of better yield of the imide complex (1) that the reaction is conducted at a temperature in a range of from 15 to 110° C. for from 6 to 48 hours.

In the production method 1, it is preferred in the point of good yield of the imide complex (1) that the reaction is conducted in argon or nitrogen atmosphere. In the raw material compound (2), it is preferred in the point of good yield that X is chlorine atom. In the raw material compound (3), it is preferred in the point of good yield that $M^2$ is lithium atom, sodium atom or potassium atom, and it is particularly preferred that $M^2$ is lithium atom.

The imide complex (1) of the invention obtained can be isolated by the ordinary post-treatment.

The raw material compound (2) in the production method 1 can easily be synthesized by reference to the known methods (for example, Inorganic Chemistry, vol. 36, p. 2647 (1997) or Journal of Chinese Chemical Society, vol. 45, p. 355 (1998)).

The production method 2 is a method for producing the imide complex (1) of the invention by the reaction between the compound (4) and the alcohol (5).

[Chem. 11]

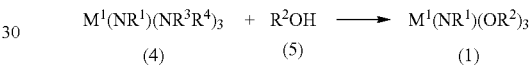

(wherein $M^1$, $R^1$, $R^3$, $R^4$ and $R^2$ are the same as defined above).

The production method 2 can be carried out in an organic solvent. Examples of the organic solvent include hydrocarbons such as pentane, hexane, heptane, octane, benzene, toluene, ethylbenzene and xylene; and ethers such as diethyl ether, diisopropyl ether, 1,2-dimethoxyethane, dioxane, tetrahydrofuran and cyclopentyl methyl ether. Those can be used alone or as mixtures thereof. Hexane or toluene is preferred in the point that yield is good.

In the production method 2, the reaction temperature is not limited. However, when the reaction is conducted at a temperature appropriately selected from a range of from –20 to 100° C., the imide complex (1) can be obtained in good yield. The reaction time is not limited. However, when the reaction is conducted in reaction time appropriately selected from a range of from 1 to 150 hours, the imide complex (1) can be obtained in good yield. It is further preferred in the point of better yield of the imide complex (1) that the reaction is conducted at a temperature in a range of from 0 to 50° C. for from 6 to 48 hours.

In the production method 2, it is preferred in the point of good yield of the imide complex (1) that the reaction is conducted in argon or nitrogen atmosphere. In the raw material compound (4), it is preferred in the point of good yield that $R^3$ and $R^4$ are simultaneously methyl group or ethyl group.

The imide complex (1) of the invention obtained can be isolated by the ordinary post-treatment.

The raw material compound (4) in the production method 2 can easily be synthesized by reference to the known methods (for example, Journal of Chinese Chemical Society, vol. 45, p. 355 (1998) or Inorganic Chemistry, vol. 22, p. 965 (1983)).

It is particularly preferred in the point of good yield that the raw material compound (4) in the production method 2 is produced by the following process. That is, the process is a method for producing the compound (4) by the reaction between the compound (2) and lithium dialkyl amide (6).

[Chem. 12]

$$M^1(NR^1)X_3(L)_r + LiNR^3R^4 \longrightarrow M^1(NR^1)(NR^3R^4)_3$$
$$(2) \qquad\qquad (6) \qquad\qquad\qquad (4)$$

(wherein $M^1$, $R^1$, X, L, r, $R^3$ and $R^4$ are the same as defined above).

This process is to obtain the compound (4) by the reaction between the compound (2) and lithium dialkyl amide (6). This reaction can be carried out in an organic solvent. Examples of the organic solvent include hydrocarbons such as pentane, hexane, heptane, octane, benzene, toluene, ethylbenzene and xylene; and ethers such as diethyl ether, diisopropyl ether, 1,2-dimethoxyethane, dioxane, tetrahydrofuran and cyclopentyl methyl ether. Those can be used alone or as mixtures thereof. It is preferred in the point of good yield to use hexane, toluene or a mixture of hexane and toluene.

In this process, the reaction temperature is not limited. However, when the reaction is conducted at a temperature appropriately selected from a range of from −80 to 100° C., the compound (4) can be obtained in good yield. The reaction time is not limited. However, when the reaction is conducted in reaction time appropriately selected from a range of from 4 to 150 hours, the compound (4) can be obtained in good yield. It is further preferred in the point of better yield that the reaction is conducted at a temperature in a range of from 0 to 50° C. for from 6 to 72 hours.

In this process, it is preferred in the point of good yield of the compound (4) that the reaction is conducted in argon or nitrogen atmosphere. In the raw material compound (2), it is preferred in the point of good yield that X is chlorine atom. In the lithium dialkyl amide (6), it is preferred in the point of good yield that $R^3$ and $R^4$ are simultaneously methyl group or ethyl group.

The compound (4) obtained by this process can be subjected as a raw material compound in the above-described production method 2 to the reaction directly without isolation. However, according to need, the compound (4) may be isolated by the ordinary post-treatment and then subjected to the reaction of the production method 2.

The production method 3 is a method for producing the imide complex (1) by the reaction between the compound (1a) and the amine (7).

[Chem. 13]

$$M^1(NR^{1a})(OR^2)_3 + R^1NH_2 \longrightarrow M^1(NR^1)(OR^2)_3$$
$$(1a) \qquad\qquad (7) \qquad\qquad (1)$$

(wherein $M^1$, $R^{1a}$, $R^2$ and $R^1$ are the same as defined above)

The production method 3 can be carried out in an organic solvent, but can be carried out without using an organic solvent. Examples of the organic solvent include hydrocarbons such as pentane, hexane, heptane, octane, benzene, toluene, ethylbenzene and xylene; and ethers such as diethyl ether, diisopropyl ether, 1,2-dimethoxyethane, dioxane, tetrahydrofuran and cyclopentyl methyl ether. Those can be used alone or as mixtures thereof. In the point of good yield, a method without using a solvent or the reaction in hexane or toluene is preferred.

In the production method 3, the reaction temperature is not limited. However, when the reaction is conducted at a temperature appropriately selected from a range of from 10 to 150° C., the imide complex (1) can be obtained in good yield. The reaction time is not limited. However, when the reaction is conducted in reaction time appropriately selected from a range of from 4 to 150 hours, the imide complex (1) can be obtained in good yield. It is further preferred in the point of better yield of the imide complex (1) that the reaction is conducted at a temperature in a range of from 20 to 50° C. for from 8 to 72 hours.

In the production method 3, it is preferred in the point of good yield of the imide complex (1) that the reaction is conducted in argon or nitrogen atmosphere.

The imide complex (1) of the invention obtained can be isolated by the ordinary post-treatment.

The production method 4 is a method for producing the imide complex (1) by reacting niobium or tantalum pentahalide (8), the alkali metal alkoxide (3) and lithium amide (9).

[Chem. 14]

$$M^1Y_5 + R^2OM^2 + R^1NHLi \longrightarrow M^1(NR^1)(OR^2)_3$$
$$(8) \qquad (3) \qquad\quad (9) \qquad\qquad (1)$$

(wherein $M^1$, Y, $R^2$, $M^2$ and $R^1$ are the same as defined above)

The production method 4 can be carried out in an organic solvent. Examples of the organic solvent include hydrocarbons such as pentane, hexane, heptane, cyclohexane, octane, benzene, toluene, ethylbenzene and xylene; and ethers such as diethyl ether, diisopropyl ether, 1,2-dimethoxyethane, dioxane, tetrahydrofuran and cyclopentyl methyl ether. Those can be used alone or as mixtures thereof. In the point of good yield, pentane, hexane, heptane and cyclohexane are preferred, and hexane is further preferred.

In the production method 4, the reaction temperature is not limited. However, when the reaction is conducted at a temperature appropriately selected from a range of from −80 to 150° C., the imide complex (1) can be obtained in good yield. The reaction time is not limited. However, when the reaction is conducted in reaction time appropriately selected from a range of from 4 to 150 hours, the imide complex (1) can be obtained in good yield. It is further preferred in the point of better yield of the imide complex (1) that the reaction is conducted at a temperature in a range of from 15 to 110° C. for from 6 to 48 hours.

In the production method 4, it is preferred in the point of good yield of the imide complex (1) that the reaction is conducted in argon or nitrogen atmosphere. Niobium tetrachloride or tantalum tetrachloride is preferred as the metal halide (8) as a raw material in the point of good yield. In the alkali metal alkoxide (3) as a raw material, it is preferred in good yield that $M^2$ is lithium atom, sodium atom or potassium atom, and lithium atom is particularly preferred. The alkali metal alkoxide (3) can be prepared by, for example, a method of reacting an alcohol $R^2OH$ and an alkali metal or a method of reacting an alcohol $R^2OH$ and alkyl lithium. The lithium amide (9) as raw material can be prepared by, for example, reacting alkyl lithium and an amine $R^1NH_2$. The alkali metal alkoxide (3) and the lithium amide (9) prepared by those methods can be used with purification or without purification. The alkali metal alkoxide (3) and the lithium amide (9) can be prepared as a mixed solution in the same system, and the mixed solution can be used as it is.

The imide complex (1) of the invention obtained can be isolated by the ordinary post-treatment.

A niobium- or tantalum-containing thin film can be produced using the imide complex (1) of the invention as a raw material. A method for producing the niobium- or tantalum-containing thin film is not particularly limited. For example, in the case of producing the niobium- or tantalum-containing thin film by CVD method or ALD method, the imide complex (1) is gasified and supplied on a substrate. The method for gasification includes a method of placing the imide complex (1) into a heated thermostatic bath, and blowing a carrier gas such as helium, neon, argon, krypton, xenon or nitrogen to gasify the same, and a method of sending the imide complex (1) as it is or in a form a solution thereof to a vaporizer, and heating to gasify the same in the vaporizer. Examples of a solvent used in the case of preparing the solution include ethers such as 1,2-dimethoxyethane, diglyme, triglyme, dioxane, tetrahydrofuran and cyclopentyl methyl ether; and hydrocarbons such as hexane, cyclohexane, methylcyclohexane, ethylcyclohexane, heptane, octane, nonane, decane, benzene, toluene, ethylbenzene and xylene.

The metal-containing thin film can be produced by a method of decomposing the imide complex (1) supplied as a gas on a substrate in the co-presence of a reactive gas such as water, oxygen or ozone, or by reacting those reactive gases with the imide complex (1) adsorbed on a substrate. The decomposition can be made with only heating, but plasma or light may additionally be used.

The present invention is described in more detail below by reference to the Examples, but the invention is not construed as being limited thereto. In the present description, Me indicates methyl group, Et indicates ethyl group, Pr indicates propyl group, $^i$Pr indicates isopropyl group, $^t$Bu indicates tert-butyl group, $^s$Bu indicates sec-butyl group, and $^t$Pe indicates tert-pentyl group. dme indicates 1,2-dimethoxyethane ligand.

REFERENCE EXAMPLE 1

Synthesis of (tert-butylimido)trichloro(1,2-dimethoxy-ethane)niobium (Nb(N$^t$Bu)Cl$_3$(dme)

3.48 g (12.9 mmol) of niobium pentachloride was suspended in 30 mL of toluene in argon atmosphere, and 2.87 g (39.2 mmol) of tert-butylamine, 1.17 g (13.0 mmol) of 1,2-dimethoxyethane and 4.22 g (31.0 mmol) of zinc (II) chloride were added in this order while cooling with ice bath. After stirring at room temperature for 12 hours, the resulting mixture was allowed to stand at –8° C. for 6 hours while cooling. Insoluble matters were filtered off, and toluene was distilled away from the filtrate under reduced pressure to obtain 3.62 g (10.0 mmol) of light yellow solid. Yield was 78%.

$^1$H NMR (500 MHz, C$_6$D$_6$, δ/ppm)

3.45 (s, 3H), 3.27 (s, 3H), 3.05 (m, 2H), 3.01 (m, 2H), 1.33 (s, 9H)

EXAMPLE 1

Synthesis of (tert-butylimido)tri(tert-butoxo)niobium (Nb(N$^t$Bu)(O$^t$Bu)$_3$)

2.24 g of tert-butanol was added to 18.9 mL of a hexane solution (1.59M) of butyllithium in argon atmosphere, and the resulting solution was stirred at room temperature for 30 minutes to prepare a lithium tert-butoxide solution. The solution was added to a solution obtained by dissolving 3.62 g (10.0 mmol) of Nb(N$^t$Bu)Cl$_3$(dme) in 15 ml of toluene, followed by stirring at room temperature for 15 hours. Insoluble matters were filtered off, and a solvent was distilled away from the filtrate under reduced pressure. The residue obtained was distilled to obtain 2.85 g of colorless liquid (yield: 74%).

$^1$H NMR (500 MHz, C$_6$D$_6$, δ/ppm)

1.38 (s, 27H), 1.37 (s, 9H)

$^{13}$C NMR (125 MHz, C$_6$D$_6$, δ/ppm)

77.5 (br), 66.2 (br), 33.8, 32.9

Thermal Analysis of Nb(N$^t$Bu)(O$^t$Bu)$_3$

The result of TG (thermogravimetric determination) measured under the condition of a temperature-rising rate of 10° C./min in an atmosphere of flowing argon in a rate of 400 ml/min, and the result of DSC (differential scanning calorimetry) measured in a temperature-rising rate of 10° C./min in a closed container are shown in FIG. 1. It was seen from TG that the material has good vaporization properties as a material of CVD method, ALD method or the like, and it was seen from DSC that the material has good thermal stability.

Measurement of Vapor Pressure of Nb(N$^t$Bu)(O$^t$Bu)$_3$

As a result of measurement of vapor pressure of Nb(N$^t$Bu)(O$^t$Bu)$_3$, the vapor pressure was 0.1 Torr at 46° C.

EXAMPLE 2

Synthesis of Nb(N$^t$Bu)(O$^t$Bu)$_3$ 810 mg (10.9 mmol) of tert-butanol was added to a solution obtained by dissolving 1.06 g (3.59 mmol) of (tert-butylimido)tris(dimethylamido)niobium (Nb(N$^t$Bu)(NMe$_2$)$_3$) in 5 ml of hexane in argon atmosphere, followed by stirring at room temperature for 24 hours. A solvent was distilled away under reduced pressure, and the residue was distilled to obtain 1.17 g of colorless liquid (yield: 85%). This liquid was dissolved in C$_6$D$_6$, and $^1$H NMR and $^{13}$C NMR spectra were measured. As a result, the same spectra as in Example 1 were obtained, and it was confirmed that the material is Nb(N$^t$Bu)(O$^t$Bu)$_3$.

EXAMPLE 3

Synthesis of Nb(N$^t$Bu)(O$^t$Bu)$_3$ 4.79 g (13.3 mmol) of Nb(N$^t$Bu)Cl$_3$(dme) was dissolved in 20 mL of toluene in argon atmosphere, and a liquid (5.3 wt %, 38.6 g, 40.1 mmol) obtained by suspending LiNMe$_2$ in hexane was added thereto, followed by stirring at room temperature for 11 hours. Insoluble matters were filtered off to obtain dark yellow solution. To analyze components contained in this dark yellow solution, a part thereof was sampled and condensed. $^1$H NMR and $^{13}$C NMR spectra of the residue obtained were measured, and it was confirmed that Nb(N$^t$Bu)(NMe$_2$)$_3$ is formed. The content of Nb(N$^t$Bu)(NMe$_2$)$_3$ in the dark yellow solution calculated based on the mass of the residue obtained was 3.15 g (process 1: yield 80%).

$^1$H NMR (500 MHz, C$_6$D$_6$, δ/ppm)

3.19 (s, 18H), 1.42 (s, 9H)

$^{13}$C NMR (125 MHz, C$_6$D$_6$, δ/ppm)

47.3, 33.7

2.37 g (32.0 mmol) of tert-butanol was added to the dark yellow solution obtained in the process 1, followed by stirring at room temperature for 6 hours. A solvent was distilled away under reduced pressure, and the residue was distilled to obtain 2.98 g of colorless liquid (process 2; yield: 73%, overall yield of processes 1 and 2: 58%). This liquid was dissolved in C$_6$D$_6$, and $^1$H NMR and $^{13}$C NMR spectra were measured. As a result, the same spectra as in Example 1 were obtained, and it was confirmed that the material is Nb(N$^t$Bu)(O$^t$Bu)$_3$.

EXAMPLE 4

Synthesis of (propylimido)tri(tert-butoxo)niobium (Nb(NPr)(O$^t$Bu)$_3$)

Figure 3:
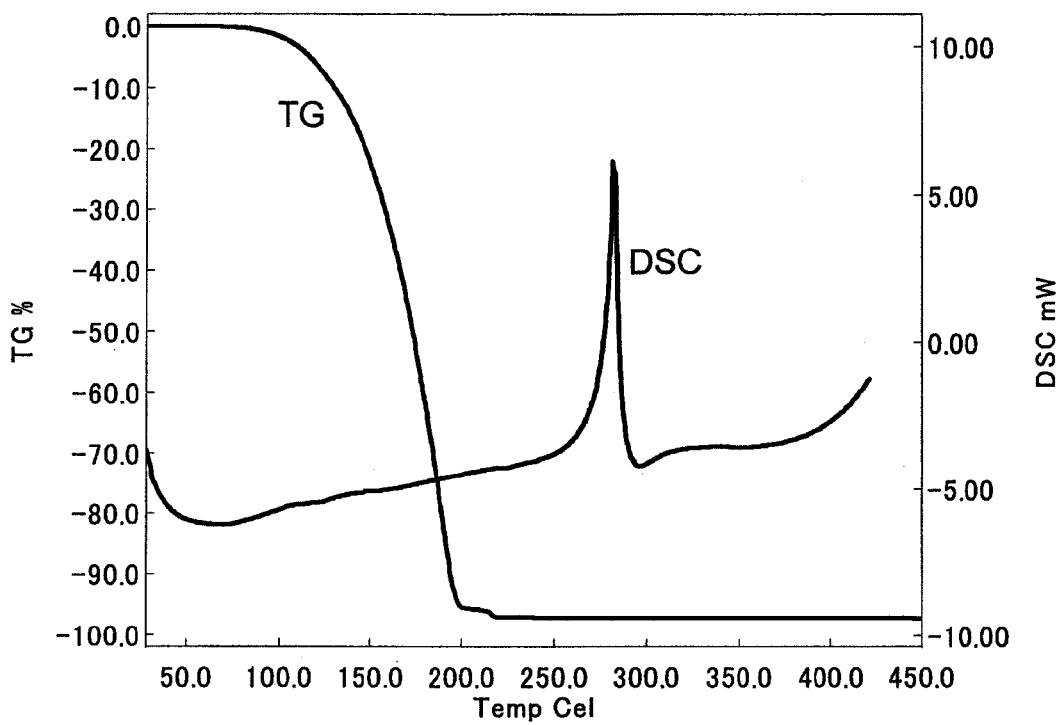
FIG. 3 is a view showing the results of TG and DSC measured in Example 4.

2.98 g (7.77 mmol) of Nb(N$^t$Bu)(O$^t$Bu)$_3$ was dissolved in 14.0 g of propylamine in argon atmosphere, followed by stirring at room temperature for 17 hours. The remaining propylamine and by-produced tert-butylamine were distilled away under reduced pressure, and the residue was distilled to obtain 2.36 g of colorless liquid (yield: 82%).
$^1$H NMR (500 MHz, C$_6$D$_6$, δ/ppm)
3.72 (br, t, J=7 Hz, 2H), 1.68 (sext, J=7 Hz, 2H), 1.39 (s, 27H), 0.91 (t, J=7 Hz, 3H)
$^{13}$C NMR (125 MHz, C$_6$D$_6$, δ/ppm)
78.0, 65.3 (br), 32.9, 27.6, 12.2
Thermal Analysis of Nb(NPr)(O$^t$Bu)$_3$
The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 3. It was seen from TG that the material has good vaporization properties as a material of CVD method, ALD method or the like, and it was seen from DSC that the material has good thermal stability.

EXAMPLE 5

Synthesis of (isopropylimido)tri(tert-butoxo)niobium (Nb(N$^i$Pr)(O$^t$Bu)$_3$)

Figure 4:
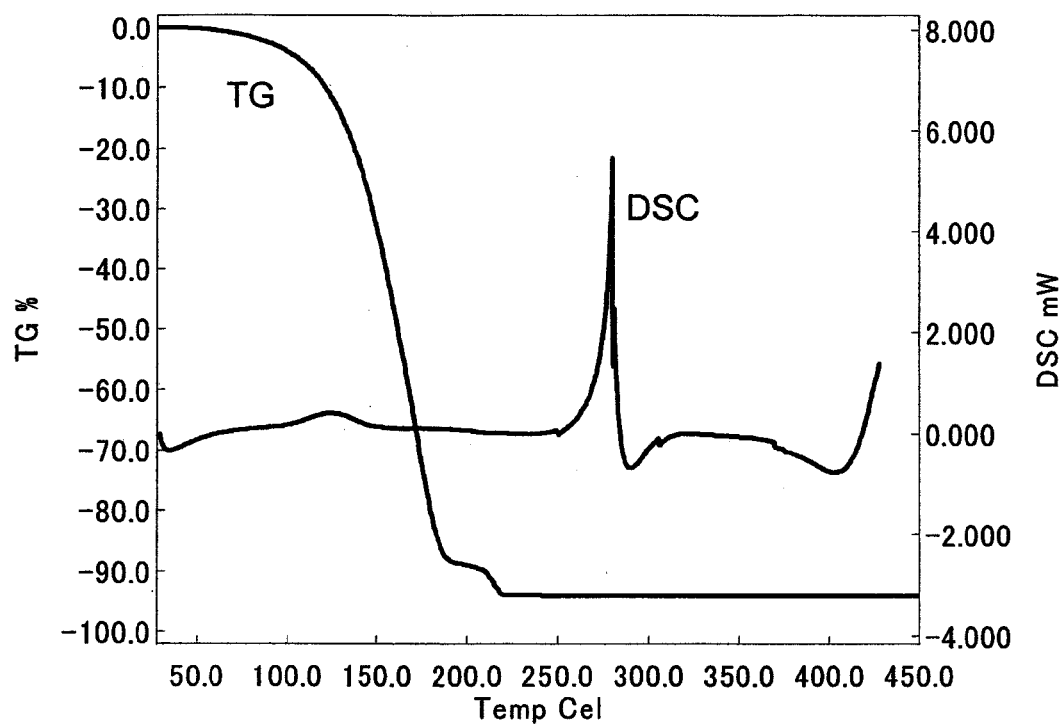
FIG. 4 is a view showing the results of TG and DSC measured in Example 5.

2.80 g (7.30 mmol) of Nb(N$^t$Bu)(O$^t$Bu)$_3$ was dissolved in mL of hexane and 13.0 g of isopropylamine in argon atmosphere, followed by stirring at room temperature for 17 hours. Hexane, the remaining isopropylamine and by-produced tert-butylamine were distilled away under reduced pressure, and the residue was distilled to obtain 2.25 g of colorless liquid (yield: 83%).
$^1$H NMR (500 MHz, C$_6$D$_6$, δ/ppm)
3.94 (br, 1H), 1.39 (s, 27H), 1.26 (d, J=7 Hz, 6H)
$^{13}$C NMR (125 MHz, C$_6$D$_6$, δ/ppm)
77.7 (br), 62.6 (br), 32.9, 27.3
Thermal Analysis of Nb(N$^i$Pr)(O$^t$Bu)$_3$
The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 4. It was seen from TG that the material has good vaporization properties as a material of CVD method, ALD method or the like, and it was seen from DSC that the material has good thermal stability.
Measurement of Vapor Pressure of Nb(N$^i$Pr)(O$^t$Bu)$_3$
As a result of measurement of vapor pressure of Nb(N$^i$Pr)(O$^t$Bu)$_3$, the vapor pressure was 0.1 Torr at 49° C.

EXAMPLE 6

Production of Nb-Containing Thin Film Using Nb(N$^t$Bu)(O$^t$Bu)$_3$

Figure 2:
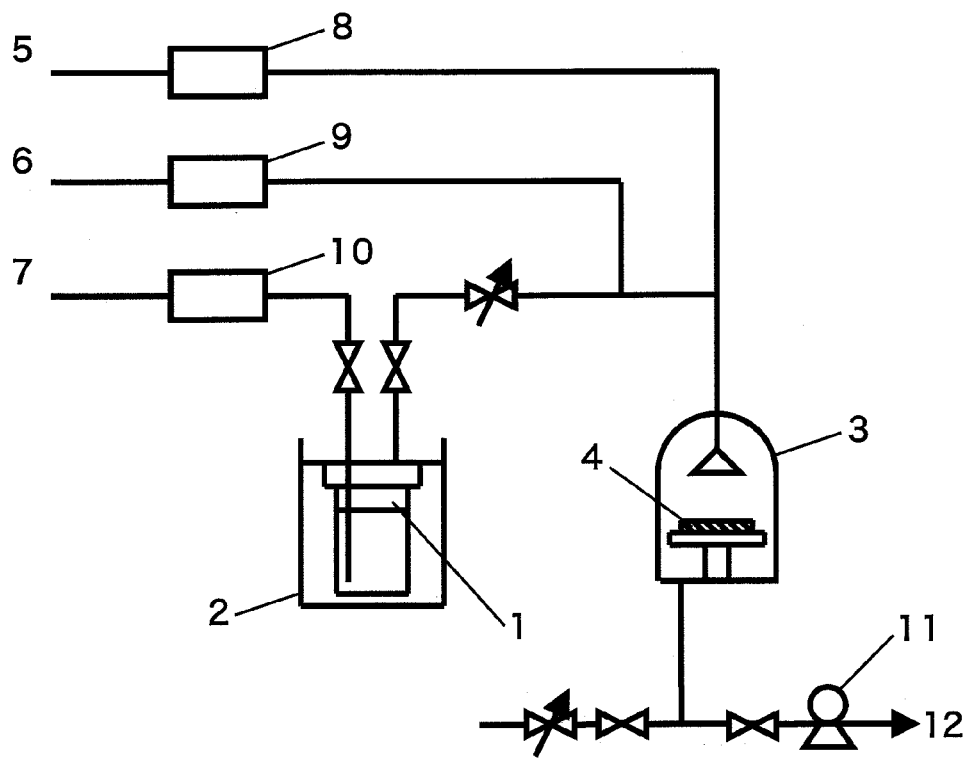
FIG. 2 is a schematic view of CVD film-forming apparatus used in Examples 6 and 57 to 64 and Comparative Examples 3 to 6.

Nb(N$^t$Bu)(O$^t$Bu)$_3$ was used as a raw material, and film formation was conducted on SiO$_2$/Si substrate for 1 hour at raw material temperature of 40° C., carrier gas (Ar) flow rate of 20 sccm, raw material pressure of 100 Torr, diluent gas (Ar) flow rate of 220 sccm, reaction gas (O$_2$) flow rate of 60 sccm, substrate temperature of 400° C. and pressure in reaction chamber of 4 Torr by CVD method using an apparatus shown in FIG. 2. The film prepared was measured with fluorescent X-ray analyzer, and as a result, characteristic X-ray of Nb was detected. Furthermore, film composition was confirmed with X-ray photoelectron spectroscopy, and as a result, it was niobium oxide. Film thickness was confirmed with SEM, and as a result, the thickness was about 40 nm.

EXAMPLE 7

Synthesis of (methylimido)tri(tert-butoxo)niobium (Nb(NMe)(O$^t$Bu)$_3$)

Figure 5:
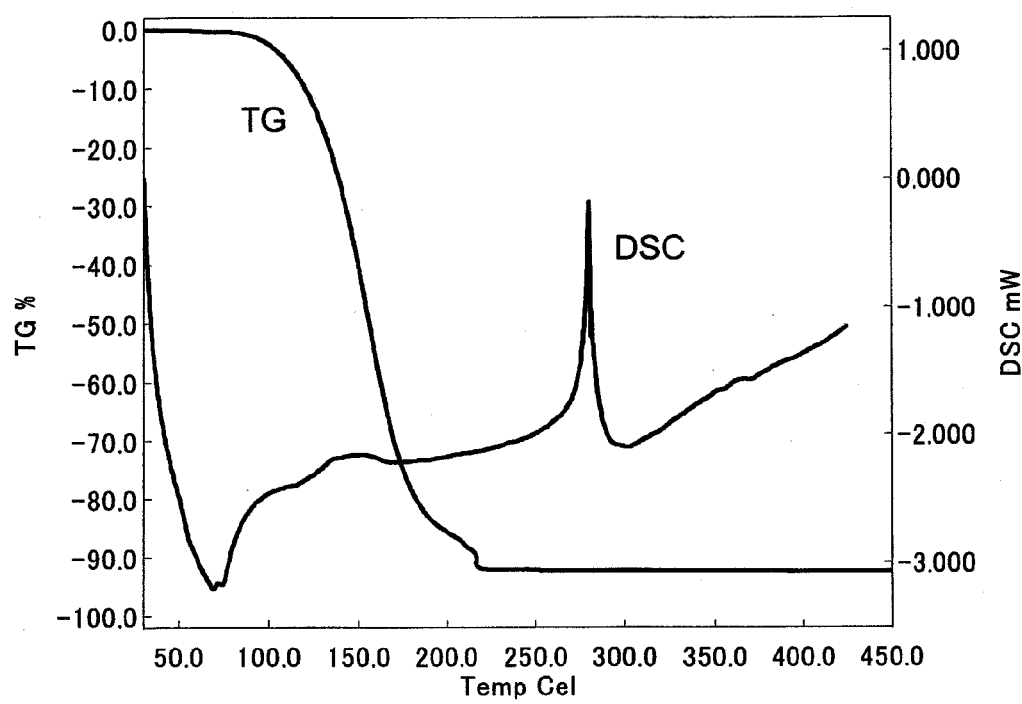
FIG. 5 is a view showing the results of TG and DSC measured in Example 7.

2.43 g (6.34 mmol) of Nb(N$^t$Bu)(O$^t$Bu)$_3$ was dissolved in a tetrahydrofuran solution (2.0M, 100 mL) of methylamine in argon atmosphere, followed by stirring at room temperature for 12 hours. A solvent and excess methylamine were distilled away under reduced pressure, and the residue was sublimated to obtain 1.22 g of white solid (yield: 56%).
$^1$H NMR (500 MHz, C$_6$D$_6$, δ/ppm)
3.55 (s, 3H), 1.38 (s, 27H)
$^{13}$C NMR (125 MHz, C$_6$D$_6$, δ/ppm)
78.2, 50.3 (br), 33.0
Thermal Analysis of Nb(NMe)(O$^t$Bu)$_3$
The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 5. It was seen from TG that the material has good vaporization properties as a material of CVD method, ALD method or the like, and it was seen from DSC that the material has good thermal stability.

REFERENCE EXAMPLE 2

Synthesis of (ethylimido)trichloro(1,2-dimethoxyethane)-niobium (Nb(NEt)Cl$_3$(dme)

10.9 g (40.2 mmol) of niobium pentachloride was suspended in 80 mL of toluene in argon atmosphere, and a solution obtained by dissolving 5.57 g (124 mmol) of ethylamine in 10 mL of toluene, 3.62 g (40.2 mmol) of 1,2-dimethoxyethane and 16.4 g (120 mmol) of zinc (II) chloride were added in this order while cooling with ice bath. After stirring at room temperature for 12 hours, the resulting mixture was allowed to stand at −8° C. for 12 hours while cooling. Insoluble matters were filtered off, and toluene was distilled away from the filtrate under reduced pressure to obtain 9.46 g (28.5 mmol) of light yellow solid.
Yield was 71%.
$^1$H NMR (500 MHz, C$_6$D$_6$, δ/ppm)
3.71 (q, J=7 Hz, 2H), 3.42 (s, 3H), 3.15 (s, 3H), 2.97 (m, 2H), 2.92 (m, 2H), 1.11 (t, J=7 Hz, 3H)

Example 8

Synthesis of (ethylimido)tri(tert-butoxo)niobium Nb(NEt)(O$^t$Bu)$_3$)

2.30 g of tert-butanol was added to 19.6 mL of a hexane solution (1.58M) of butyllithium in argon atmosphere, and the resulting solution was stirred at room temperature for 30 minutes to prepare a lithium tert-butoxide solution. The solution was added to a solution obtained by dissolving 3.44 g (10.4 mmol) of Nb(NEt)Cl$_3$(dme) in 15 ml of toluene, followed by stirring at room temperature for 12 hours. Insoluble matters were filtered off, and a solvent was distilled away from the filtrate under reduced pressure. The residue obtained was distilled to obtain 3.41 g of colorless liquid (yield: 93%).

$^1$H NMR (500 MHz, $C_6D_6$, δ/ppm)

3.72 (q, J=7 Hz, 2H), 1.35 (s, 27H), 1.20 (t, J=7 Hz, 3H)

$^{13}$C NMR (125 MHz, $C_6D_6$, δ/ppm)

77.9, 57.6 (br), 32.9, 19.7

Thermal Analysis of Nb(NEt)(O$^t$Bu)$_3$

Figure 6:
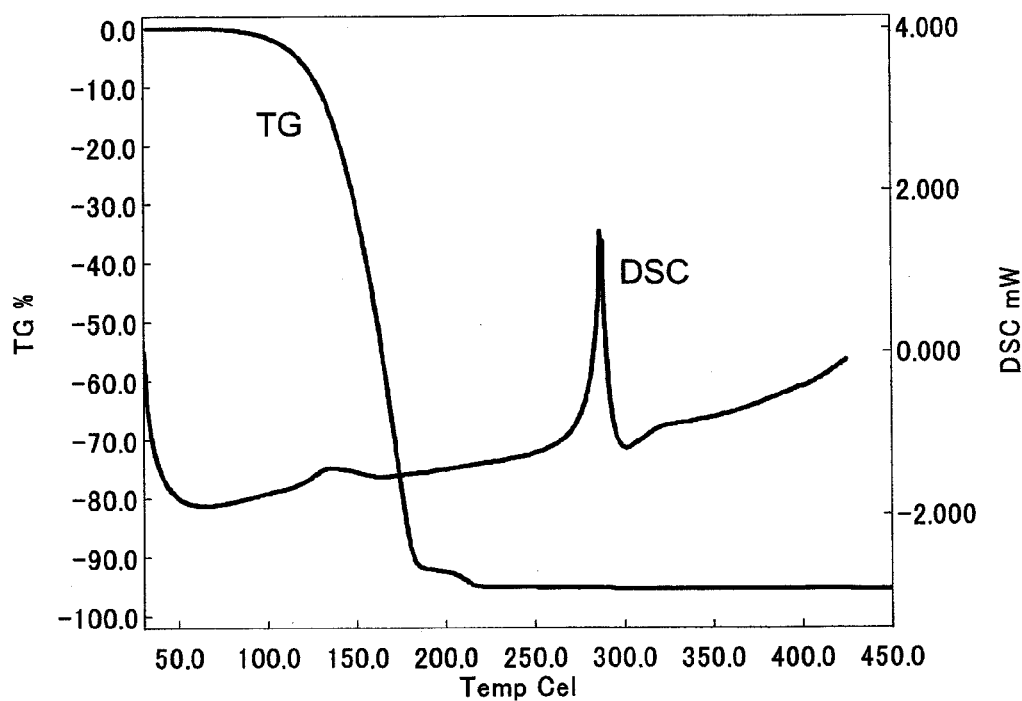
FIG. 6 is a view showing the results of TG and DSC measured in Example 8.

The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 6. It was seen from TG that the material has good vaporization properties as a material of CVD method, ALD method or the like, and it was seen from DSC that the material has good thermal stability.

EXAMPLE 9

Synthesis of (ethylimido)tri(tert-pentyloxo)niobium (Nb(NEt)(O$^t$Pe)$_3$)

2.26 g of tert-pentanol was added to 16.2 mL of a hexane solution (1.58M) of butyllithium in argon atmosphere, and the resulting solution was stirred at room temperature for 30 minutes to prepare a lithium tert-pentyl oxide solution. The solution was added to a solution obtained by dissolving 2.85 g (8.57 mmol) of Nb(NEt)Cl$_3$(dme) in 12 ml of toluene, followed by stirring at room temperature for 12 hours. Insoluble matters were filtered off, and a solvent was distilled away from the filtrate under reduced pressure. The residue obtained was distilled to obtain 3.09 g of colorless liquid (yield: 91%).

$^1$H NMR (500 MHz, $C_6D_6$, δ/ppm)

3.69 (q, J=7 Hz, 2H), 1.58 (q, J=8 Hz, 6H), 1.30 (s, 18H), 1.18 (t, J=7 Hz, 3H), 0.95 (t, J=8 Hz, 9H)

$^{13}$C NMR (125 MHz, $C_6D_6$, δ/ppm)

80.0, 57.5 (br), 37.8, 30.6, 19.6, 9.3

Thermal Analysis of Nb(NEt)(O$^t$Pe)$_3$

Figure 7:
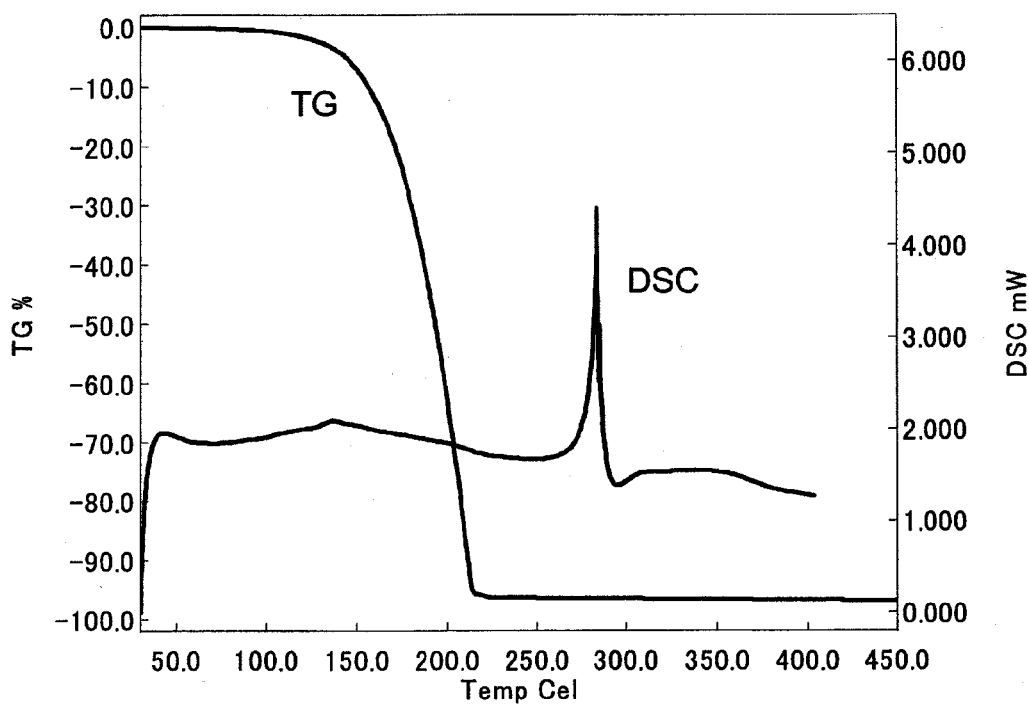
FIG. 7 is a view showing the results of TG and DSC measured in Example 9.

The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 7. It was seen from TG that the material has good vaporization properties as a material of CVD method, ALD method or the like, and it was seen from DSC that the material has good thermal stability.

EXAMPLE 10

Synthesis of (ethylimido)tri(1-ethyl-1-methylpropyloxo)-niobium (Nb(NEt)(OCEt$_2$Me)$_3$)

2.35 g of 3-methyl-3-pentanol was added to 14.5 mL of a hexane solution (1.58M) of butyllithium in argon atmosphere, and the resulting solution was stirred at room temperature for 30 minutes to prepare a lithium 1-ethyl-1-methylpropyl oxide solution. The solution was added to a solution obtained by dissolving 2.55 g (7.68 mmol) of Nb(NEt)Cl$_3$(dme) in 10 ml of toluene, followed by stirring at room temperature for 12 hours. Insoluble matters were filtered off, and a solvent was distilled away from the filtrate under reduced pressure. The residue obtained was distilled to obtain 2.67 g of colorless liquid (yield: 79%).

$^1$H NMR (500 MHz, $C_6D_6$, δ/ppm)

3.72 (q, J=7 Hz, 2H), 1.62 (m, 12H), 1.32 (s, 9H), 1.20 (t, J=7 Hz, 3H), 0.98 (t, J=8 Hz, 18H)

$^{13}$C NMR (125 MHz, $C_6D_6$, δ/ppm)

82.2, 57.5 (br), 35.5, 27.6, 19.5, 9.1

Thermal Analysis of Nb(NEt)(OCEt$_2$Me)$_3$

Figure 8:
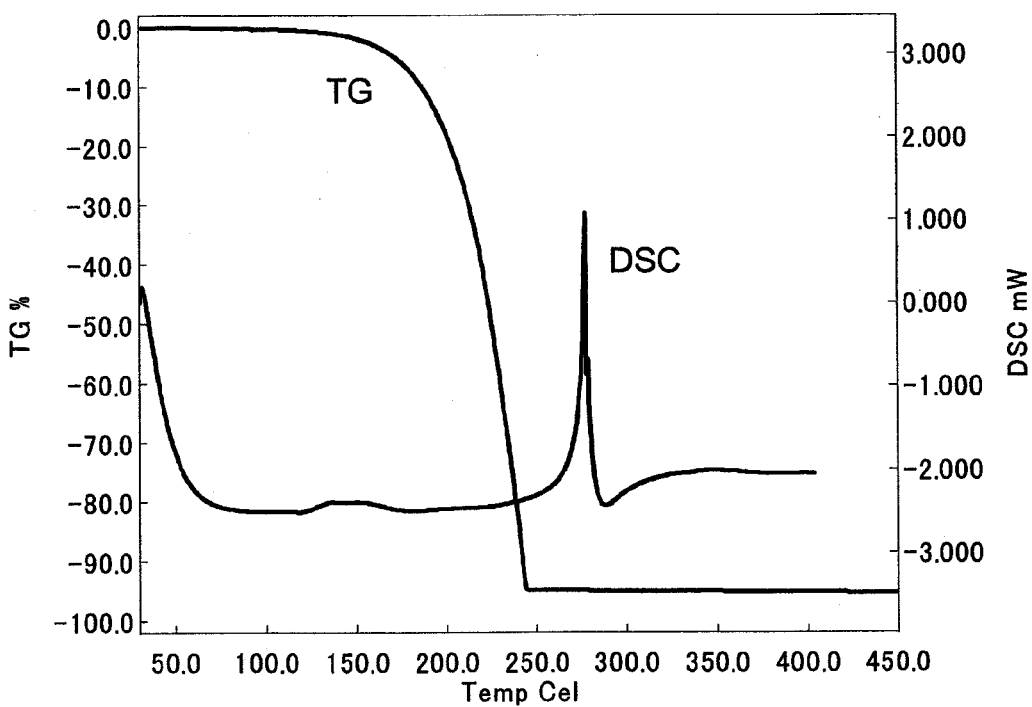
FIG. 8 is a view showing the results of TG and DSC measured in Example 10.

The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 8. It was seen from TG that the material has good vaporization properties as a material of CVD method, ALD method or the like, and it was seen from DSC that the material has good thermal stability.

EXAMPLE 11

Synthesis of (tert-butylimido)tri(tert-pentyloxo)niobium (Nb(N$^t$Bu)(O$^t$Pe)$_3$)

754 mg of tert-pentanol was added to 5.40 mL of a hexane solution (1.58M) of butyllithium in argon atmosphere, and the resulting solution was stirred at room temperature for 30 minutes to prepare a lithium tert-pentyl oxide solution. The solution was added to a solution obtained by dissolving 1.03 g (2.85 mmol) of Nb(N$^t$Bu)Cl$_3$(dme) in 5 ml of toluene, followed by stirring at room temperature for 6 hours. Insoluble matters were filtered off, and a solvent was distilled away from the filtrate under reduced pressure. The residue obtained was distilled to obtain 1.11 g of colorless liquid (yield: 91%).

$^1$H NMR (500 MHz, $C_6D_6$, δ/ppm)

1.60 (q, J=8 Hz, 6H), 1.34 (s, 9H), 1.32 (s, 18H), 0.95 (t, J=8 Hz, 9H)

$^{13}$C NMR (125 MHz, $C_6D_6$, δ/ppm)

79.5 (br), 66.0 (br), 37.7, 33.7, 30.7, 9.4

Thermal Analysis of Nb(N$^t$Bu)(O$^t$Pe)$_3$

Figure 9:
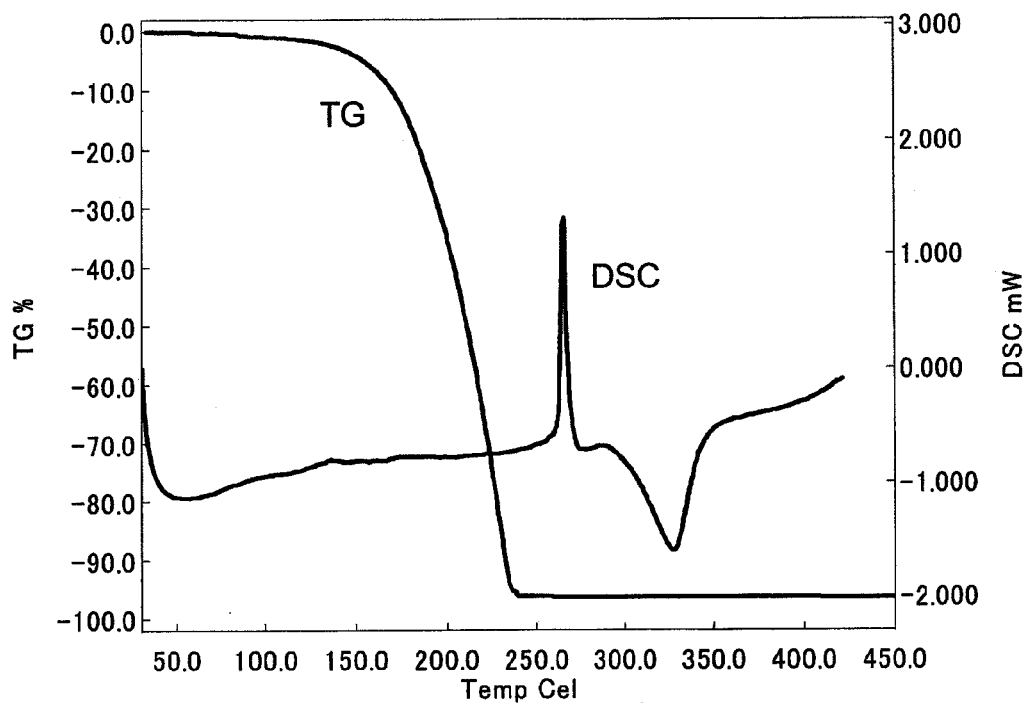
FIG. 9 is a view showing the results of TG and DSC measured in Example 11.

The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 9. It was seen from TG that the material has good vaporization properties as a material of CVD method, ALD method or the like, and it was seen from DSC that the material has good thermal stability.

EXAMPLE 12

Synthesis of (tert-pentylimido)tri(tert-butoxo)niobium (Nb(N$^t$Pe)(O$^t$Bu)$_3$)

1.86 g of tert-butanol was added to 15.8 mL of a hexane solution (1.58M) of butyllithium in argon atmosphere, and the resulting solution was stirred at room temperature for 30 minutes to prepare a lithium tert-butoxide solution. The solution was added to a solution obtained by dissolving 3.13 g (8.37 mmol) of (tert-pentylimido)trichloro(1,2-dimethoxyethane)niobium (Nb(N$^t$Pe)Cl$_3$(dme) in 12 ml of toluene, followed by stirring at room temperature for 8 hours. Insoluble matters were filtered off, and a solvent was distilled away from the filtrate under reduced pressure. The residue obtained was distilled to obtain 2.73 g of colorless liquid (yield: 82%).

$^1$H NMR (500 MHz, $C_6D_6$, δ/ppm)

1.66 (q, J=8 Hz, 2H), 1.39 (s, 27H), 1.33 (s, 6H), 1.06 (t, J=8 Hz, 3H)

$^{13}$C NMR (125 MHz, $C_6D_6$, δ/ppm)

77.7 (br), 69.0 (br), 38.6, 32.9, 31.1, 10.4

Thermal Analysis of Nb(N$^t$Pe)(O$^t$Bu)$_3$

Figure 10:
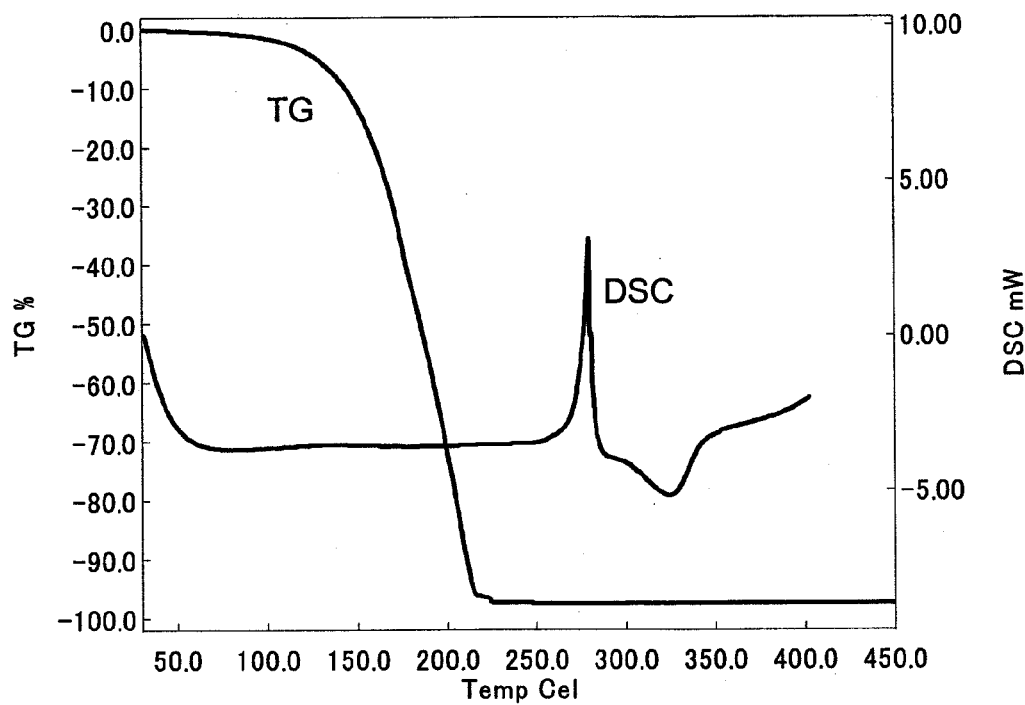
FIG. 10 is a view showing the results of TG and DSC measured in Example 12.

The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 10. It was seen from TG that the material has good vaporization properties as a material of CVD method, ALD method or the like, and it was seen from DSC that the material has good thermal stability.

EXAMPLE 13

Synthesis of (1,1,3,3-tetramethylbutylimido)tri(tert-butoxo)niobium (Nb(NCMe$_2$CH$_2$CMe$_3$)(O$^t$Bu)$_3$)

6.16 g of tert-butanol was added to 52.6 mL of a hexane solution (1.58M) of butyllithium in argon atmosphere, and the resulting solution was stirred at room temperature for 1 hour to prepare a lithium tert-butoxide solution. The solution was added to a solution obtained by dissolving 11.53 g (27.7 mmol) of (1,1,3,3-tetramethylbutylimido)tri-chloro(1,2-dimethoxyethane)niobium (Nb(NCMe$_2$CH$_2$Me$_3$)Cl$_3$(dme)) in 50 ml of toluene, followed by stirring at room temperature for 12 hours. Insoluble matters were filtered off, and a solvent was distilled away from the filtrate under reduced pressure. The residue obtained was distilled to obtain 9.94 g of pale yellow liquid (yield: 82%).

Figure 11:
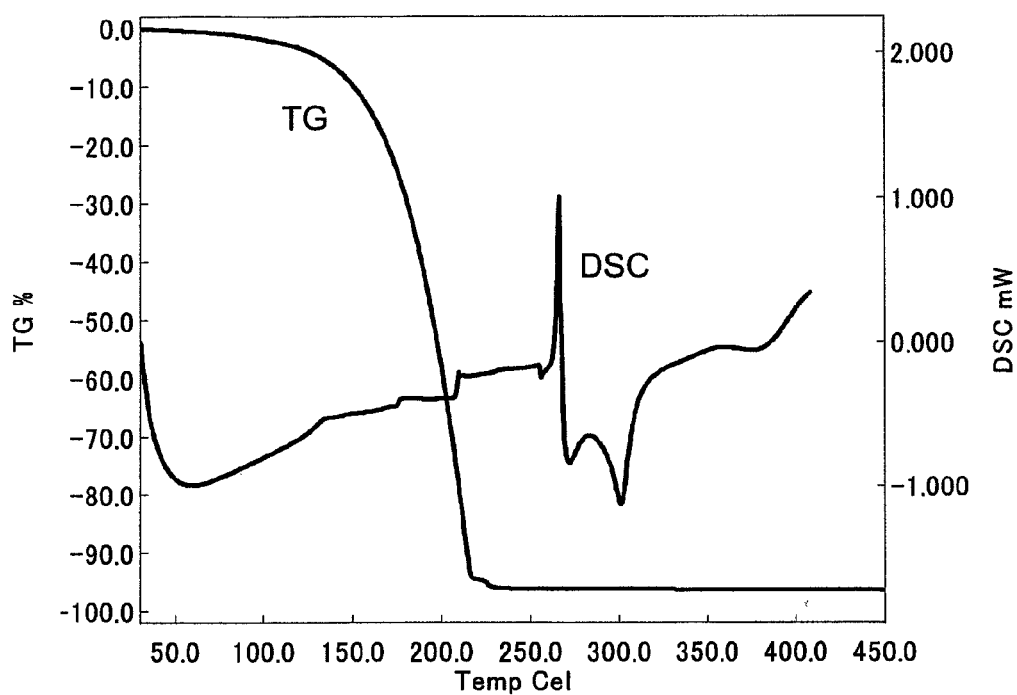
FIG. 11 is a view showing the results of TG and DSC measured in Example 13.

$^1$H NMR (500 MHz, C$_6$D$_6$, δ/ppm)
1.88 (s, 2H), 1.48 (s, 6H), 1.40 (s, 27H), 1.09 (s, 9H)
$^{13}$C NMR (125 MHz, C$_6$D$_6$, δ/ppm)
77.8 (br), 70.1 (br), 59.0, 33.3, 32.9, 32.3, 31.9
Thermal Analysis of Nb(NCMe$_2$CH$_2$CMe$_3$)(O$^t$Bu)$_3$ The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 11. It was seen from TG that the material has good vaporization properties as a material of CVD method, ALD method or the like, and it was seen from DSC that the material has good thermal stability.

EXAMPLE 14

Synthesis of Nb(N$^t$Bu)(O$^t$Bu)$_3$ 2.96 g (8.21 mmol) of Nb(N$^t$Bu)Cl$_3$(dme) was added to 15 ml of toluene in argon atmosphere, and slurry obtained by suspending 2.77 g (24.6 mmol) of potassium tert-butoxide in 15 mL of hexane was added thereto, followed by stirring at room temperature for 15 hours. Insoluble matters were filtered off, and a solvent was distilled away from the filtrate under reduced pressure. The residue obtained was distilled to obtain 1.79 g of colorless liquid (yield: 57%). This liquid was dissolved in C$_6$D$_6$, and $^1$H NMR and $^{13}$C NMR spectra were measured. As a result, the same spectra as in Example 1 were obtained, and it was confirmed that the material is Nb(N$^t$Bu)(O$^t$Bu)$_3$.

EXAMPLE 15

Synthesis of Nb(N$^t$Bu)(O$^t$Bu)$_3$ 4.95 g (13.7 mmol) of Nb(N$^t$Bu)Cl$_3$(dme) was dissolved in 25 ml of toluene in argon atmosphere, and slurry obtained by suspending 3.96 g (41.2 mmol) of sodium tert-butoxide in 25 mL of hexane was added thereto, followed by stirring at room temperature for 15 hours. Insoluble matters were filtered off, and a solvent was distilled away from the filtrate under reduced pressure. The residue obtained was distilled to obtain 1.44 g of colorless liquid (yield: 27%). This liquid was dissolved in C$_6$D$_6$, and $^1$H NMR and $^{13}$C NMR spectra were measured. As a result, the same spectra as in Example 1 were obtained, and it was confirmed that the material is Nb(N$^t$Bu)(O$^t$Bu)$_3$.

EXAMPLE 16

Synthesis of (ethylimido)tri(tert-pentyloxo)tantalum (Ta(NEt)(O$^t$Pe)$_3$)

871 mg (9.88 mmol) of tert-pentanol was added to a solution obtained by dissolving 1.45 g (3.29 mmol) of (ethylimido)tris(diethylamido)tantalum (Ta(NEt)(NEt$_2$)$_3$) in 7 ml of toluene in argon atmosphere, followed by stirring at room temperature for 18 hours. A solvent was distilled away under reduced pressure, and the residue was distilled to obtain 1.19 g of white solid (yield: 74%).

$^1$H NMR (500 MHz, C$_6$D$_6$, δ/ppm)
4.11 (q, J=7 Hz, 2H), 1.63 (m, 12H), 1.31 (s, 9H), 1.26 (t, J=7 Hz, 3H), 0.97 (t, J=8 Hz, 18H)

EXAMPLE 17

Synthesis of (ethylimido)tri(1-ethyl-1-methylpropyloxo)-tantalum (Ta(NEt)(OCEt$_2$Me)$_3$)

1.02 g (9.98 mmol) of 3-methyl-3-pentanol was added to a solution obtained by dissolving 1.46 g (3.32 mmol) of Ta(NEt)(NEt$_2$)$_3$ in 7 ml of toluene in argon atmosphere, followed by stirring at room temperature for 12 hours. A solvent was distilled away under reduced pressure, and the residue was sublimated to obtain 1.52 g of colorless liquid (yield: 87%).

Figure 12:
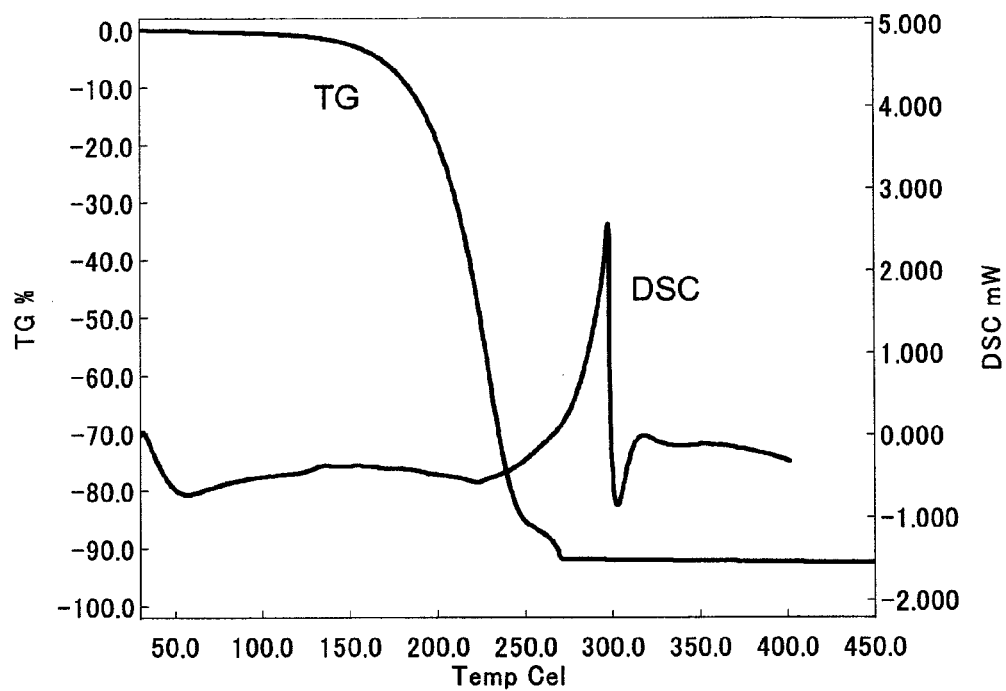
FIG. 12 is a view showing the results of TG and DSC measured in Example 17.

$^1$H NMR (500 MHz, C$_6$D$_6$, δ/ppm)
4.11 (q, J=7 Hz, 2H), 1.63 (m, 12H), 1.31 (s, 9H), 1.26 (t, J=7 Hz, 3H), 0.97 (t, J=8 Hz, 18H)
$^{13}$C NMR (125 MHz, C$_6$D$_6$, δ/ppm)
82.4, 55.6, 35.5, 27.7, 21.2, 9.0
Thermal Analysis of Ta(NEt)(OCEt$_2$Me)$_3$ The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 12. It was seen from TG that the material has good vaporization properties as a material of CVD method, ALD method or the like, and it was seen from DSC that the material has good thermal stability.

REFERENCE EXAMPLE 3

Synthesis of (isopropylimido)trichlorodipyridine tantalum (Ta(N$^i$Pr)Cl$_3$(pyridine)$_2$)

3.82 g (10.7 mmol) of tantalum pentachloride was suspended in a mixed liquid of 25 mL of toluene and 5 mL of diethyl ether in argon atmosphere, and 2.61 g of sodium metasilicate and 1.26 g of isopropylamine were added in this order. After stirring at room temperature for 10 hours, 7.0 mL of pyridine was added, followed by further stirring for 12 hours. Insoluble matters were filtered off, and a solvent and excess pyridine were distilled away from the filtrate under reduced pressure to obtain 3.36 g (6.69 mmol) of yellowish white solid. Yield was 63%.

$^1$H NMR (500 MHz, C$_6$D$_6$, δ/ppm)

9.18 (br, 2H), 8.83 (d, J=7 Hz, 2H), 6.83 (br, 1H), 6.67 (t, J=7 Hz, 1H), 6.51 (br, 2H), 6.28 (t, J=7 Hz, 2H), 5.23 (sept, J=7 Hz, 1H), 1.40 (d, J=7 Hz, 6H)

EXAMPLE 18

Synthesis of (isopropylimido)tri(tert-butoxo)tantalum (Ta(N$^i$Pr)(O$^t$Bu)$_3$)

1.49 g of tert-butanol was added to 12.7 mL of a hexane solution (1.58M) of butyllithium in argon atmosphere, and the resulting solution was stirred at room temperature for 30 minutes to prepare a lithium tert-butoxide solution. The solution was added to a solution obtained by dissolving 3.36 g (6.68 mmol) of Ta(N$^i$Pr)Cl$_3$(pyridine)$_2$ in 15 ml of toluene, followed by stirring at room temperature for 12 hours. Insoluble matters were filtered off, and a solvent was distilled away from the filtrate under reduced pressure. The residue obtained was distilled to obtain 2.65 g of colorless liquid (yield: 87%).

$^1$H NMR (500 MHz, C$_6$D$_6$, δ/ppm)
4.31 (sept, J=7 Hz, 1H), 1.38 (s, 27H), 1.31 (d, J=7 Hz, 6H)
$^{13}$C NMR (125 MHz, C$_6$D$_6$, δ/ppm)
78.1, 61.0, 32.9, 28.9

Thermal Analysis of Ta(N$^i$Pr)(O$^t$Bu)$_3$

Figure 13:
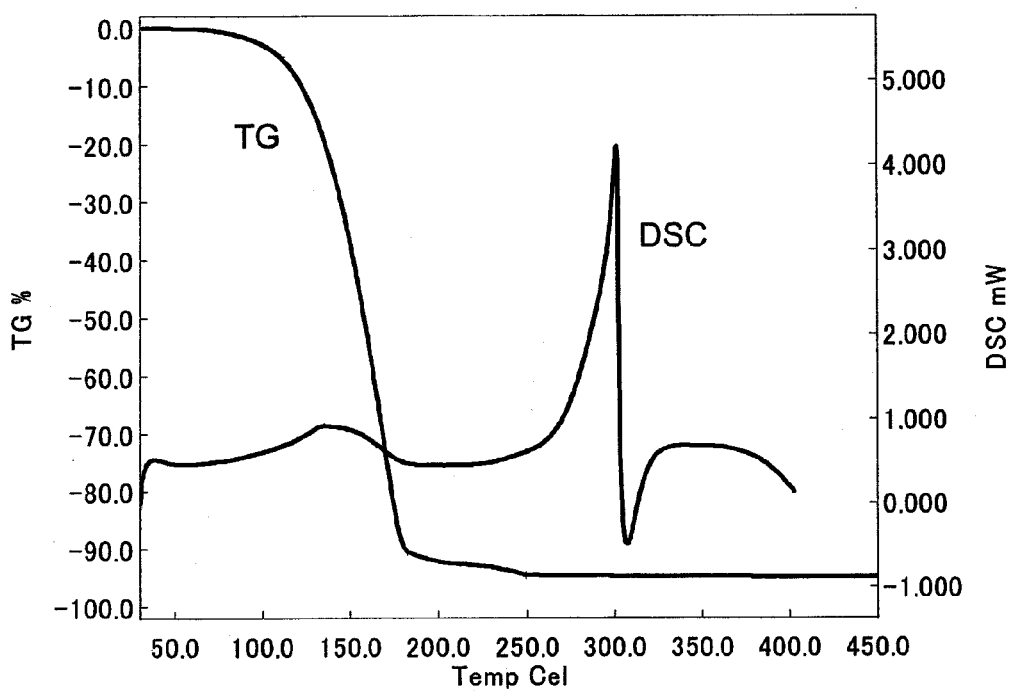
FIG. 13 is a view showing the results of TG and DSC measured in Example 18.

The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 13. It was seen from TG that the material has good vaporization properties as a material of CVD method, ALD method or the like, and it was seen from DSC that the material has good thermal stability.

Measurement of Vapor Pressure of Ta(N$^i$Pr)(O$^t$Bu)$_3$

As a result of measurement of vapor pressure of Ta(N$^i$Pr)(O$^t$Bu)$_3$, the vapor pressure was 0.1 Torr at 47° C.

REFERENCE EXAMPLE 4

Synthesis of (isopropylimido)trichloro(1,2-dimethoxy-ethane)tantalum (Ta(N$^i$Pr)Cl$_3$(dme))

5.87 g (16.4 mmol) of tantalum pentachloride was suspended in 60 mL of toluene in argon atmosphere, and 2.90 g (49.1 mmol) of isopropylamine, 1.48 g (16.4 mmol) of 1,2-dimethoxyethane and 5.80 g (42.6 mmol) of zinc (II) chloride were added in this order while cooling with ice bath. After stirring at room temperature for 12 hours, the resulting mixture was allowed to stand at −8° C. for 22 hours while cooling. Insoluble matters were filtered off, and toluene was distilled away from the filtrate under reduced pressure to obtain 4.67 g (10.7 mmol) of pale yellow solid.

Yield was 66%.
$^1$H NMR (500 MHz, C$_6$D$_6$, δ/ppm)
4.88 (sept, J=7 Hz, 1H), 3.52 (s, 3H), 3.49 (s, 3H), 3.21 (m, 2H), 3.18 (m, 2H), 1.25 (d, J=7 Hz, 6H)

EXAMPLE 19

Synthesis of Ta(N$^i$Pr)(O$^t$Bu)$_3$ 2.39 g of tert-butanol was added to 20.5 mL of a hexane solution (1.57M) of butyllithium in argon atmosphere, and the resulting solution was stirred at room temperature for 30 minutes to prepare a lithium tert-butoxide solution. The solution was added to a solution obtained by dissolving 4.67 g (10.7 mmol) of Ta(N$^i$Pr)Cl$_3$(dme) in 17 ml of toluene, followed by stirring at room temperature for 12 hours. Insoluble matters were filtered off, and a solvent was distilled away from the filtrate under reduced pressure. The residue obtained was distilled to obtain 3.23 g of colorless liquid (yield: 66%). This liquid was dissolved in C$_6$D$_6$, and $^1$H NMR and $^{13}$C NMR spectra were measured. As a result, the same spectra as in Example 18 were obtained, and it was confirmed that the material is Ta(N$^i$Pr)(O$^t$Bu)$_3$.

REFERENCE EXAMPLE 5

Synthesis of (propylimido)trichloro(1,2-dimethoxy-ethane)-tantalum (Ta(NPr)Cl$_3$(dme))

5.86 g (16.4 mmol) of tantalum pentachloride was suspended in 50 mL of toluene in argon atmosphere, and 2.91 g (49.2 mmol) of propylamine, 1.48 g (16.4 mmol) of 1,2-dimethoxyethane and 5.36 g (39.3 mmol) of zinc (II) chloride were added in this order while cooling with ice bath. After stirring at room temperature for 12 hours, the resulting mixture was allowed to stand at −8° C. for 24 hours while cooling. Insoluble matters were filtered off, and toluene was distilled away from the filtrate under reduced pressure to obtain 3.39 g (7.80 mmol) of white solid.

Yield was 48%.
$^1$H NMR (500 MHz, C$_6$D$_6$, δ/ppm)
4.67 (t, J=6 Hz, 1H), 3.41 (s, 3H), 3.31 (s, 3H), 2.94 (s, 4H), 1.63 (m, 2H), 1.11 (t, J=7 Hz, 3H)

EXAMPLE 20

Synthesis of (propylimido)tri(tert-butoxo)tantalum Ta(NPr)(O$^t$Bu)$_3$ 1.74 g of tert-butanol was added to 14.7 mL of a hexane solution (1.59M) of butyllithium in argon atmosphere, and the resulting solution was stirred at room temperature for 4 hours to prepare a lithium tert-butoxide solution. The solution was added to a solution obtained by dissolving 3.39 g (7.80 mmol) of Ta(NPr)Cl$_3$(dme) in 14 ml of toluene, followed by stirring at room temperature for 18 hours. Insoluble matters were filtered off, and a solvent was distilled away from the filtrate under reduced pressure. The residue obtained was distilled to obtain 2.50 g of colorless liquid (yield: 70%).

$^1$H NMR (500 MHz, C$_6$D$_6$, δ/ppm)
4.71 (m, 2H), 2.06 (m, 2H), 1.48 (s, 27H), 1.09 (t, J=7 Hz, 3H)
$^{13}$C NMR (125 MHz, C$_6$D$_6$, δ/ppm)
78.6, 65.4, 32.8, 28.7, 12.2

EXAMPLE 21

Synthesis of (tert-butylimido)tri(tert-butoxo)tantalum (Ta(N$^t$Bu)(O$^t$Bu)$_3$)

9.26 g of tert-butanol was added to 79.0 mL of a hexane solution (1.58M) of butyllithium in argon atmosphere, and the resulting solution was stirred at room temperature for 12 hours to prepare a lithium tert-butoxide solution. The solution was added to a solution obtained by dissolving 18.6 g (41.6 mmol) of (tert-butylimido)trichloro(1,2-dimethoxyethane) tantalum Ta(N$^t$Bu)Cl$_3$(dme) in 80 ml of toluene, followed by stirring at room temperature for 6 hours. Insoluble matters were filtered off, and a solvent was distilled away from the filtrate under reduced pressure. The residue obtained was distilled to obtain 14.5 g of colorless liquid (yield: 74%).

$^1$H NMR (500 MHz, C$_6$D$_6$, δ/ppm)

1.43 (s, 9H), 1.38 (s, 27H)
$^{13}$C NMR (125 MHz, C$_6$D$_6$, δ/ppm)
77.9, 64.4, 35.3, 33.0

Thermal Analysis of Ta(N$^t$Bu)(O$^t$Bu)$_3$

Figure 14:
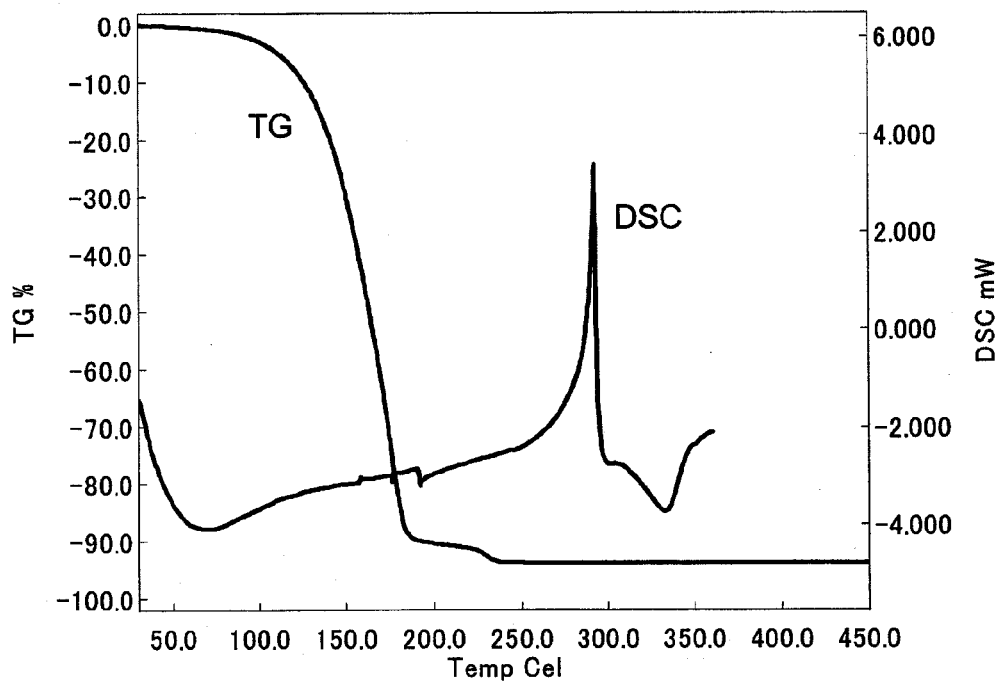
FIG. 14 is a view showing the results of TG and DSC measured in Example 21.

The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 14. It was seen from TG that the material has good vaporization properties as a material of CVD method, ALD method or the like, and it was seen from DSC that the material has good thermal stability.

Measurement of Vapor Pressure of Ta(N$^t$Bu)(O$^t$Bu)$_3$

As a result of measurement of vapor pressure of Ta(N$^t$Bu)(O$^t$Bu)$_3$, the vapor pressure was 0.1 Torr at 50° C.

EXAMPLE 22

Synthesis of Ta(N$^t$Bu)(O$^t$Bu)$_3$ 1.68 g of tert-butanol was added to 14.3 mL of a hexane solution (1.58M) of butyllithium in argon atmosphere, and the resulting solution was stirred at room temperature for 30 minutes to prepare a lithium tert-butoxide solution. The solution was added to a solution obtained by dissolving 3.90 g (7.55 mmol) of (tert-butylimido)trichlorodipyridine tantalum (Ta(N$^t$Bu)Cl$_3$(pyridine)$_2$) in 15 ml of toluene, followed by stirring at room temperature for 6 hours. Insoluble matters were filtered off, and a solvent was distilled away from the filtrate under reduced pressure. The residue obtained was distilled to obtain 2.60 g of colorless liquid (yield: 73%). This liquid was dissolved in C$_6$D$_6$, and $^1$H NMR and $^{13}$C NMR spectra were measured. As a result, the same spectra as in Example 21 were obtained, and it was confirmed that the material is Ta(N$^t$Bu)(O$^t$Bu)$_3$.

EXAMPLE 23

Synthesis of (tert-butylimido)tri(tert-pentyloxo)tantalum (Ta(N$^t$Bu)(O$^t$Pe)$_3$)

1.42 g (16.1 mmol) of tert-pentanol was added to a solution obtained by dissolving 2.52 g (5.38 mmol) of (tert-butylimido)tris(diethylamido)tantalum (Ta(N$^t$Bu)(NEt$_2$)$_3$) in 8 mL of hexane in argon atmosphere, followed by stirring at room temperature for 12 hours. A solvent was distilled away under reduced pressure, and the residue was distilled to obtain 2.57 g of colorless liquid (yield: 93%).

$^1$H NMR (500 MHz, C$_6$D$_6$, δ/ppm)
1.62 (q, J=7 Hz, 6H), 1.41 (s, 9H), 1.35 (s, 18H), 0.96 (t, J=7 Hz, 9H)
$^{13}$C NMR (125 MHz, C$_6$D$_6$, δ/ppm)
80.0, 64.4, 37.7, 35.2, 30.7, 9.3

Thermal Analysis of Ta(N$^t$Bu)(O$^t$Pe)$_3$

Figure 15:
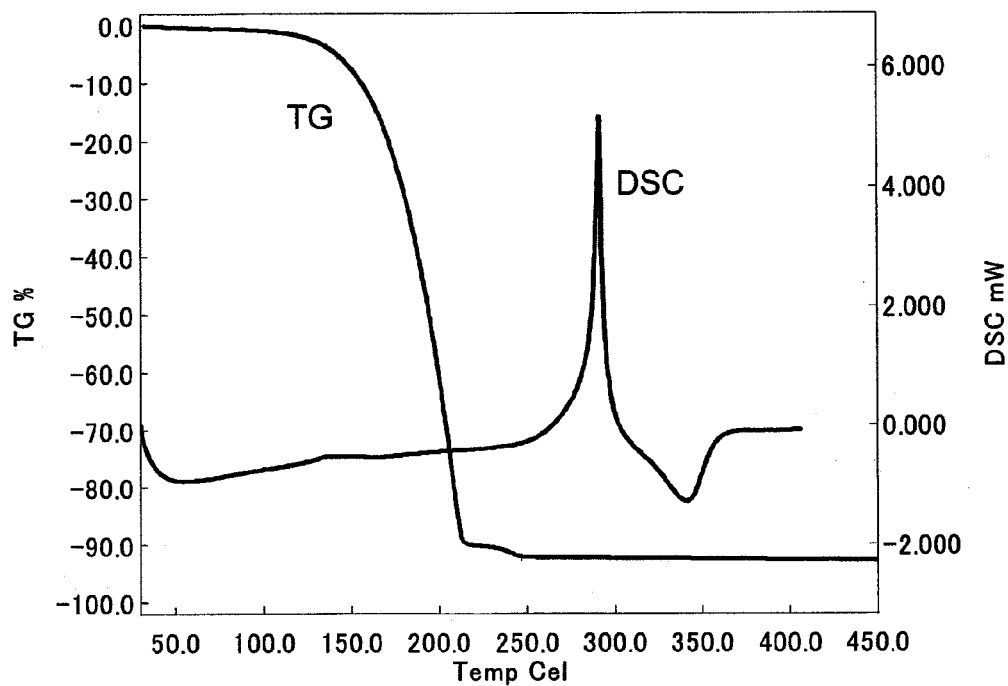
FIG. 15 is a view showing the results of TG and DSC measured in Example 23.

The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 15. It was seen from TG that the material has good vaporization properties as a material of CVD method, ALD method or the like, and it was seen from DSC that the material has good thermal stability.

EXAMPLE 24

Synthesis of (tert-butylimido)tris(1,1-diethylpropyloxo)-tantalum (Ta(N$^t$Bu)(OCEt$_3$)$_3$)

1.05 g (9.04 mmol) of 3-ethyl-3-pentanol was added to a solution obtained by dissolving 1.40 g (3.00 mmol) of Ta(N$^t$Bu)(NEt$_2$)$_3$ in 4 mL of hexane in argon atmosphere, followed by stirring at room temperature for 12 hours. A solvent was distilled away under reduced pressure, and the residue was distilled to obtain 1.56 g of colorless liquid (yield: 87%).

$^1$H NMR (500 MHz, C$_6$D$_6$, δ/ppm)
1.66 (q, J=8 Hz, 18H), 1.41 (s, 9H), 0.94 (t, J=8 Hz, 27H)
$^{13}$C NMR (125 MHz, C$_6$D$_6$, δ/ppm)
84.2, 64.6, 35.0, 32.2, 8.8

Thermal Analysis of Ta(N$^t$Bu)(OCEt$_3$)$_3$

Figure 16:
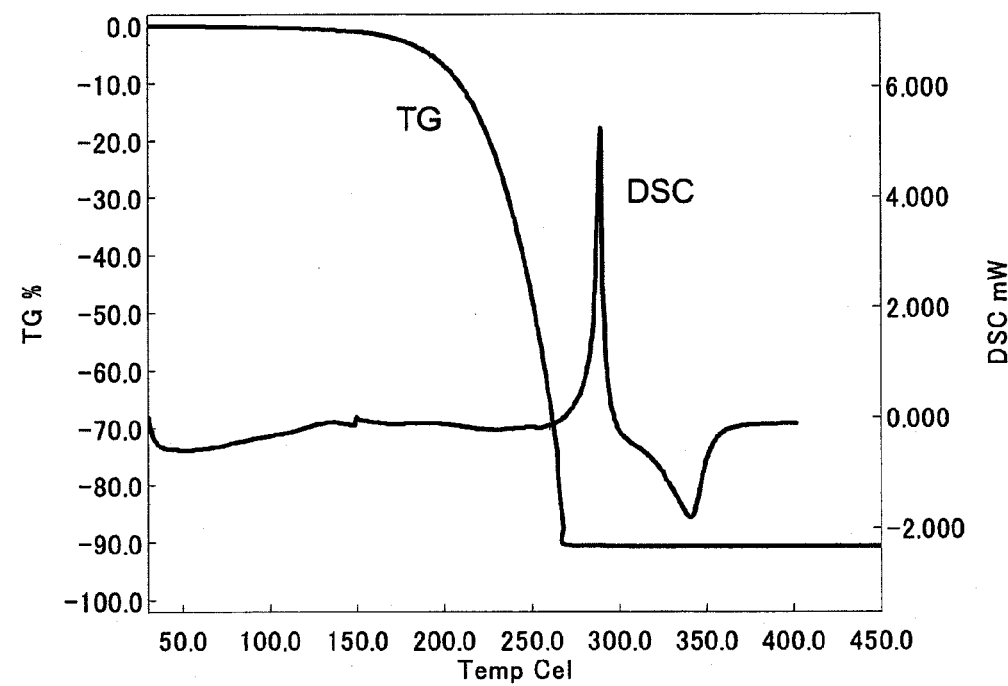
FIG. 16 is a view showing the results of TG and DSC measured in Example 24.

The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 16. It was seen from TG that the material has good vaporization properties as a material of CVD method, ALD method or the like, and it was seen from DSC that the material has good thermal stability.

EXAMPLE 25

Synthesis of (tert-pentylimido)tri(tert-butoxo)tantalum (Ta(N$^t$Pe)(O$^t$Bu)$_3$)

1.58 g of tert-butanol was added to 13.6 mL of a hexane solution (1.57M) of butyllithium in argon atmosphere, and the resulting solution was stirred at room temperature for 1 hour to prepare a lithium tert-butoxide solution. The solution was added to a solution obtained by suspending 3.77 g (7.11 mmol) of (tert-pentylimido)trichlorodipyridine tantalum (Ta(N$^t$Pe)Cl$_3$(pyridine)$_2$) in 10 ml of toluene, followed by stirring at room temperature for 6 hours. Insoluble matters were filtered off, and a solvent was distilled away from the filtrate under reduced pressure. The residue obtained was distilled to obtain 2.66 g of colorless liquid (yield: 77%).

$^1$H NMR (500 MHz, C$_6$D$_6$, δ/ppm)
1.67 (q, J=8 Hz, 2H), 1.37 (s, 27H), 1.36 (s, 6H), 1.10 (t, J=8 Hz, 3H)
$^{13}$C NMR (125 MHz, C$_6$D$_6$, δ/ppm)
78.1, 66.8, 39.8, 32.9, 32.7, 10.4

Thermal Analysis of Ta(N$^t$Pe)(O$^t$Bu)$_3$

Figure 17:
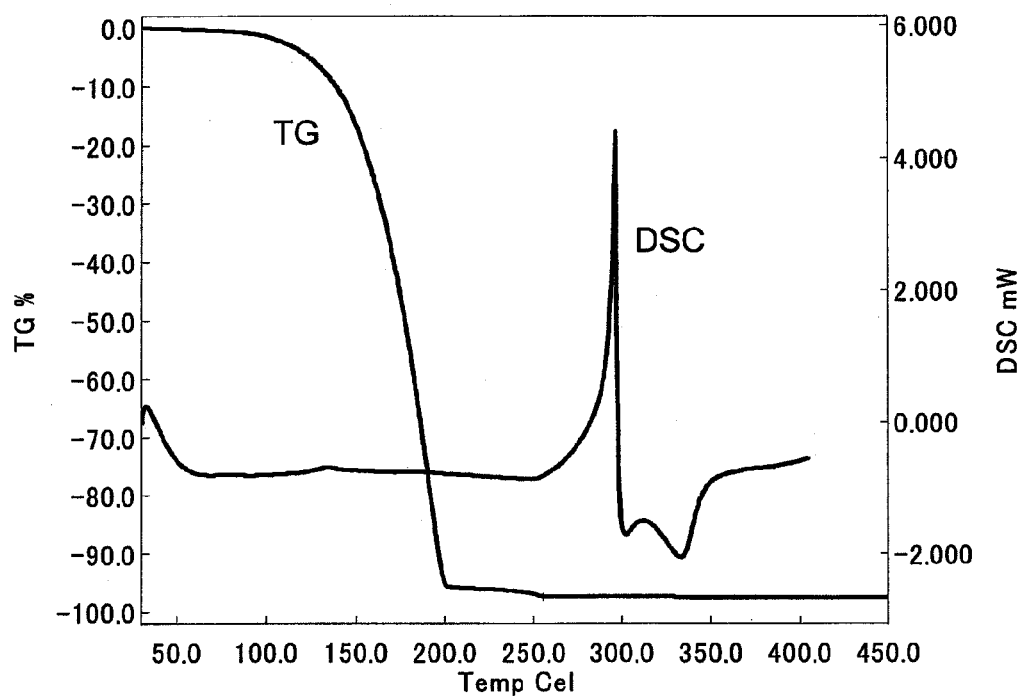
FIG. 17 is a view showing the results of TG and DSC measured in Example 25.

The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 17. It was seen from TG that the material has good vaporization properties as a material of CVD method, ALD method or the like, and it was seen from DSC that the material has good thermal stability.

EXAMPLE 26

Synthesis of (1,1,3,3-tetramethylbutylimido)tri(tert-butoxo)tantalum (Ta(NCMe$_2$CH$_2$CMe$_3$)(O$^t$Bu)$_3$)

1.73 g of tert-butanol was added to 14.9 mL of a hexane solution (1.57M) of butyllithium in argon atmosphere, and the resulting solution was stirred at room temperature for 1 hour to prepare a lithium tert-butoxide solution. The solution was added to a solution obtained by suspending 4.47 g (7.80 mmol) of (1,1,3,3-tetramethylbutylimido)tri-chlorodipyridine tantalum (Ta(NCMe$_2$CH$_2$CMe$_3$)Cl$_3$(pyridine)$_2$) in 10 ml of toluene, followed by stirring at room temperature for 6 hours. Insoluble matters were filtered off, and a solvent was distilled away from the filtrate under reduced pressure. The residue obtained was distilled to obtain 3.26 g of pale yellow liquid (yield: 80%).

$^1$H NMR (500 MHz, C$_6$D$_6$, δ/ppm)

Figure 18:
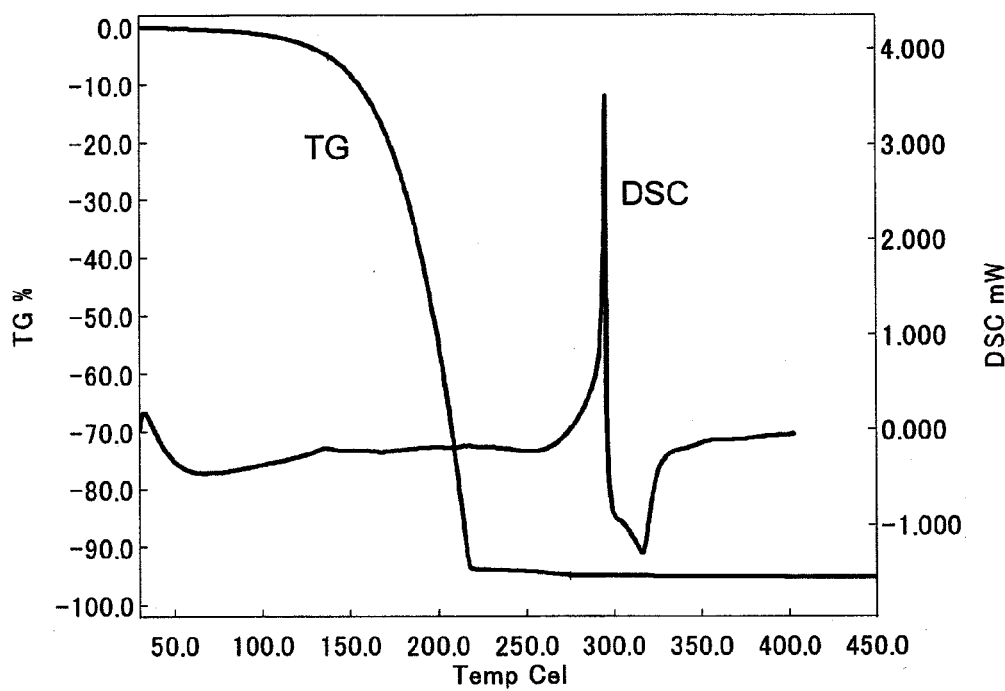
FIG. 18 is a view showing the results of TG and DSC measured in Example 26.

1.88 (s, 2H), 1.50 (s, 6H), 1.39 (s, 27H), 1.12 (s, 9H)
$^{13}$C NMR (125 MHz, C$_6$D$_6$, δ/ppm)
78.2, 68.3, 60.7, 34.9, 33.0, 32.4, 32.0
Thermal Analysis of Ta(NCMe$_2$CH$_2$CMe$_3$)(O$^t$Bu)$_3$ The result of TG measured under the condition of a temperature-rising rate of 10° C./min in an atmosphere of flowing argon in a rate of 400 ml/min, and the result of DSC measured in a temperature-rising rate of 10° C./min in a closed container are shown in FIG. 18. It was seen from TG that the material has good vaporization properties as a material of CVD method, ALD method or the like, and it was seen from DSC that the material has good thermal stability.

COMPARATIVE EXAMPLE 1

Thermal Analysis of Nb(OEt)$_5$

Figure 19:
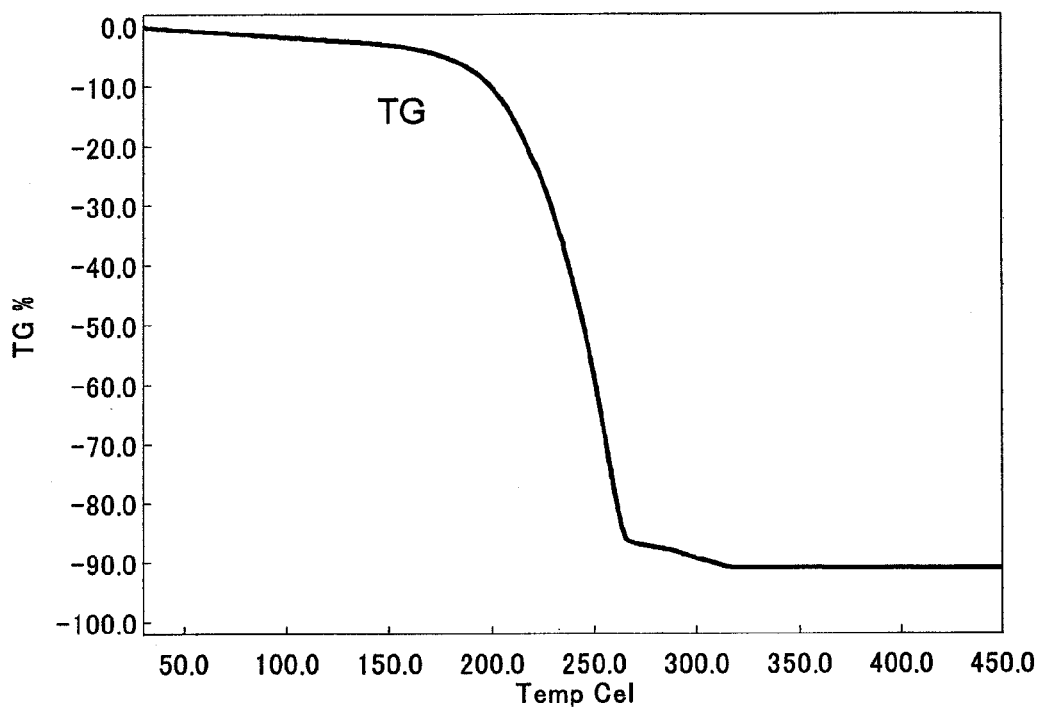
FIG. 19 is a view showing the result of TG measured in Comparative Example 1.

The result of TG measured under the condition of a temperature-rising rate of 10° C./min in an atmosphere of flowing argon in a rate of 400 ml/min is shown in FIG. 19. It is apparent that vaporization properties are poor as compared with the imide complex (1) of the invention.
Measurement of Vapor Pressure of Nb(OEt)$_5$ As a result of measurement of vapor pressure of Nb(OEt)$_5$, the vapor pressure was 0.1 Torr at 120° C.

COMPARATIVE EXAMPLE 2

Thermal Analysis of Ta(OEt)$_5$

Figure 20:
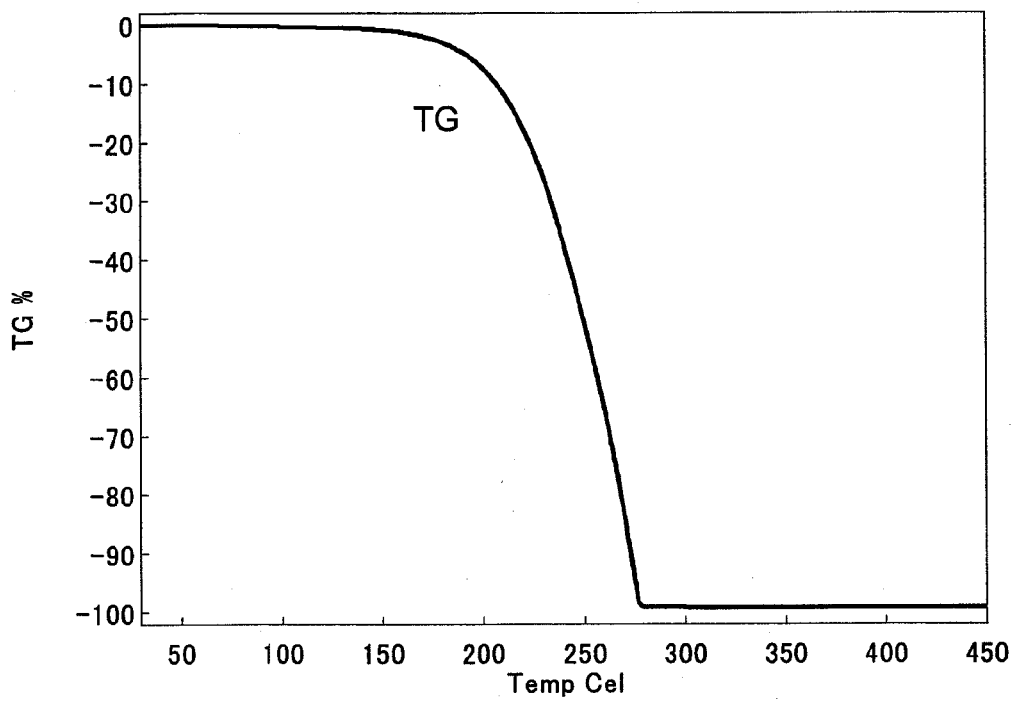
FIG. 20 is a view showing the result of TG measured in Comparative Example 2.

The result of TG measured under the condition of a temperature-rising rate of 10° C./min in an atmosphere of flowing argon in a rate of 400 ml/min is shown in FIG. 20. It is apparent that vaporization properties are poor as compared with the imide complex (1) of the invention.
Measurement of Vapor Pressure of Ta(OEt)$_5$ As a result of measurement of vapor pressure of Ta(OEt)$_5$, the vapor pressure was 0.1 Torr at 129° C.

EXAMPLE 27

Synthesis of (methylimido)tris(1-ethyl-1-methylpropyloxo)-niobium (Nb(NMe)(OCEt$_2$Me)$_3$)

2.41 g of 3-methyl-3-pentanol and 9.8 mL of a tetrahydrofuran solution (2.0M) of methylamine were added to 23.8 mL of a hexane solution (1.65M) of butyllithium in argon atmosphere, and the resulting mixture was stirred at room temperature for 1 hour, followed by drying under reduced pressure. 20 mL of hexane was added to the remaining white solid to prepare slurry. The slurry was added to a hexane (5 mL) suspension of 2.13 g (7.87 mmol) of niobium pentachloride, followed by stirring at room temperature for 12 hours. Insoluble matters were filtered off, and a solvent was distilled away from the filtrate under reduced pressure. The residue obtained was distilled under reduced pressure to obtain 1.70 g of colorless liquid (yield: 51%).
$^1$H NMR (500 MHz, C$_6$D$_6$, δ/ppm)
3.52 (s, 3H), 1.16-1.55 (m, 12H), 1.30 (s, 9H), 0.97 (t, J=8 Hz, 18H)
$^{13}$C NMR (125 MHz, C$_6$D$_6$, δ/ppm)
82.5, 49.8 (br), 35.5, 27.7, 9.0

EXAMPLE 28

Synthesis of (ethylimido)tris(1,1-diethylpropyloxo)niobium (Nb(NEt)(OCEt$_3$)$_3$)

2.75 g of 3-ethyl-3-pentanol and 1.22 g of a toluene solution (70 wt %) of ethylamine were added to 23.9 mL of a hexane solution (1.65M) of butyllithium in argon atmosphere, and the resulting mixture was stirred at room temperature for 10 hours, followed by drying under reduced pressure. 20 mL of hexane was added to the remaining white solid to prepare slurry. The slurry was added to a hexane (5 mL) suspension of 2.13 g (7.90 mmol) of niobium pentachloride, followed by stirring at room temperature for 12 hours. Insoluble matters were filtered off, and a solvent was distilled away from the filtrate under reduced pressure. The residue obtained was distilled under reduced pressure to obtain 3.14 g of colorless liquid (yield: 83%).
$^1$H NMR (500 MHz, C$_6$D$_6$, δ/ppm)
3.71 (br, 2H), 1.64 (q, J=8 Hz, 18H), 1.19 (t, J=7 Hz, 3H), 0.95 (t, J=8 Hz, 27H)
$^{13}$C NMR (125 MHz, C$_6$D$_6$, δ/ppm)
84.3, 57.0 (br), 32.2, 19.4, 8.7

EXAMPLE 29

Synthesis of (isopropylimido)tris(1-ethyl-1-methylpropyl-oxo)niobium (Nb(N$^i$Pr)(OCEt$_2$Me)$_3$)

2.36 g of 3-methyl-3-pentanol and 909 mg of isopropylamine were added to 23.3 mL of a hexane solution (1.65M) of butyllithium in argon atmosphere, followed by stirring at room temperature for 12 hours. This solution was added to a hexane (5 mL) suspension of 2.08 g (7.70 mmol) of niobium pentachloride, followed by stirring at room temperature for 14 hours. Insoluble matters were filtered off, and a solvent was distilled away from the filtrate under reduced pressure. The residue obtained was distilled under reduced pressure to obtain 2.22 g of colorless liquid (yield: 64%).
$^1$H NMR (500 MHz, C$_6$D$_6$, δ/ppm)
3.91 (br, 1H), 1.61 (m, 12H), 1.30 (s, 9H), 1.22 (d, J=7 Hz, 6H), 0.96 (t, J=8 Hz, 18H)
$^{13}$C NMR (125 MHz, C$_6$D$_6$, δ/ppm)
82.0, 62.5 (br), 35.5, 27.7, 27.1, 9.1

EXAMPLE 30

Synthesis of Nb(N$^i$Pr)(O$^t$Bu)$_3$ 1.57 g of isopropylamine was added to 16.1 mL of a hexane solution (1.65M) of butyllithium in argon atmosphere, followed by stirring at room temperature for 4 hours. This solution was added to a hexane (10 mL) suspension of 3.58 g mmol) of niobium pentachloride, followed by stirring at room temperature for 7 hours. A lithium tert-butoxide solution prepared by adding 2.95 g of tert-butanol to 24.1 mL of a hexane solution (1.65M) of butyllithium and stirring for 11 hours was further added, followed by stirring at room temperature for 14 hours. Insoluble matters were filtered off, and a solvent was distilled away from the filtrate under reduced pressure. The residue obtained was distilled under reduced pressure to obtain 3.14 g of colorless liquid (yield: 64%). This liquid was dissolved in C$_6$D$_6$, and $^1$H NMR and $^{13}$C NMR spectra were measured. As a result, it was confirmed that the material is Nb(N$^i$Pr)(O$^t$Bu)$_3$.

EXAMPLE 31

Synthesis of Nb(N$^t$Bu)(O$^t$Bu)$_3$ 4.58 g of tert-butanol and 3.02 g of tert-butylamine were added to 62.4 mL of a hexane solution (1.65M) of butyllithium in argon atmosphere, followed by stirring at room temperature for 11 hours. This solution was added to a hexane (20 mL) suspension of 5.56 g (20.6 mmol) of niobium pentachloride, followed by stirring at room temperature for 24 hours. Insoluble matters were filtered off, and a solvent was distilled away from the filtrate under reduced pressure. The residue obtained was distilled under reduced pressure to obtain 6.04 g of colorless liquid (yield: 77%). This liquid was dissolved in $C_6D_6$, and $^1H$ NMR and $^{13}C$ NMR spectra were measured. As a result, it was confirmed that the material is $Nb(N^tBu)(O^tBu)_3$.

EXAMPLE 32

Synthesis of $Nb(N^tBu)(O^tBu)_3$ 2.27 g of tert-butanol and 1.49 g of tert-butylamine were added to 30.9 mL of a hexane solution (1.65M) of butyllithium in argon atmosphere, followed by stirring at room temperature for 12 hours. This solution was added to a solution obtained by suspending 5.02 g (10.2 mmol) of niobium pentabromide in 10 mL of hexane, followed by stirring at room temperature for 24 hours. Insoluble matters were filtered off, and a solvent was distilled away from the filtrate under reduced pressure. The residue obtained was distilled under reduced pressure to obtain 1.56 g of colorless liquid (yield: 40%). This liquid was dissolved in $C_6D_6$, and $^1H$ NMR and $^{13}C$ NMR spectra were measured. As a result, it was confirmed that the material is $Nb(N^tBu)(O^tBu)_3$.

EXAMPLE 33

Synthesis of $Nb(N^tBu)(O^tBu)_3$ 2.29 g of tert-butylamine was added to 19.0 mL of a hexane solution (1.65M) of butyllithium in argon atmosphere, followed by stirring at room temperature for 11 hours. This solution was added to a hexane (10 mL) suspension of 4.23 g (15.7 mmol) of niobium pentachloride, followed by stirring at room temperature for 10 minutes. 4.52 g of sodium tert-butoxide was further added, followed by stirring for 24 hours. Insoluble matters were filtered off, and a solvent was distilled away from the filtrate under reduced pressure. The residue obtained was distilled under reduced pressure to obtain 4.37 g of colorless liquid (yield: 73%). This liquid was dissolved in $C_6D_6$, and $^1H$ NMR and $^{13}C$ NMR spectra were measured. As a result, it was confirmed that the material is $Nb(N^tBu)(O^tBu)_3$.

EXAMPLE 34

Synthesis of $Nb(N^tBu)(O^tPe)_3$ 2.32 g of tert-pentanol and 1.28 g of tert-butylamine were added to 26.5 mL of a hexane solution (1.65M) of butyllithium in argon atmosphere, followed by stirring at room temperature for 12 hours. This solution was added to a hexane (10 mL) suspension of 2.37 g (8.76 mmol) of niobium pentachloride, followed by stirring at room temperature for 24 hours. Insoluble matters were filtered off, and a solvent was distilled away from the filtrate under reduced pressure. The residue obtained was distilled under reduced pressure to obtain 2.93 g of colorless liquid (yield: 79%). This liquid was dissolved in $C_6D_6$, and $^1H$ NMR and $^{13}C$ NMR spectra were measured. As a result, it was confirmed that the material is $Nb(N^tBu)(O^tPe)_3$.

EXAMPLE 35

Synthesis of (tert-butylimido)tris(1,1-diethylpropyloxo)-niobium ($Nb(N^tBu)(OCEt_3)_3$)

2.78 g of 3-ethyl-3-pentanol and 1.17 g of tert-butylamine were added to 24.2 mL of a hexane solution (1.65M) of butyllithium in argon atmosphere, followed by stirring at room temperature for 12 hours. This solution was added to a hexane (10 mL) suspension of 2.16 g (7.98 mmol) of niobium pentachloride, followed by stirring at room temperature for 24 hours. Insoluble matters were filtered off, and a solvent was distilled away from the filtrate under reduced pressure. The residue obtained was distilled under reduced pressure to obtain 3.33 g of colorless liquid (yield: 82%).
$^1H$ NMR (500 MHz, $C_6D_6$, δ/ppm)
1.65 (q, J=8 Hz, 18H), 1.35 (s, 9H), 0.95 (t, J=8 Hz, 27H)
$^{13}C$ NMR (125 MHz, $C_6D_6$, δ/ppm)
84.1, 66.4 (br), 33.5, 32.2, 8.9

EXAMPLE 36

Synthesis of $Nb(N^tPe)(O^tBu)_3$ 1.69 g of tert-butanol and 1.33 g of tert-pentylamine were added to 23.1 mL of a hexane solution (1.65M) of butyllithium in argon atmosphere, followed by stirring at room temperature for 12 hours. This solution was added to a hexane (5 mL) suspension of 2.06 g (7.62 mmol) of niobium pentachloride, followed by stirring at room temperature for 24 hours. Insoluble matters were filtered off, and a solvent was distilled away from the filtrate under reduced pressure. The residue obtained was distilled under reduced pressure to obtain 2.19 g of colorless liquid (yield: 72%). This liquid was dissolved in $C_6D_6$, and $^1H$ NMR and $^{13}C$ NMR spectra were measured. As a result, it was confirmed that the material is $Nb(N^tPe)(O^tBu)_3$.

EXAMPLE 37

Synthesis of (1,3-dimethylbutylimido)tris(tert-butoxo)-niobium ($Nb(NCHMeCH_2CHMe_2)(O^tBu)_3$)

1.95 g of tert-butanol and 1.78 g of 1,3-dimethylbutylamine were added to 26.6 mL of a hexane solution (1.65M) of butyllithium in argon atmosphere, followed by stirring at room temperature for 12 hours. This solution was added to a hexane (5 mL) suspension of 2.37 g (8.78 mmol) of niobium pentachloride, followed by stirring at room temperature for 24 hours. Insoluble matters were filtered off, and a solvent was distilled away from the filtrate under reduced pressure. The residue obtained was distilled under reduced pressure to obtain 1.58 g of pale yellow liquid (yield: 44%).
$^1H$ NMR (500 MHz, $C_6D_6$, δ/ppm)
3.90 (br, 1H), 1.93 (m, 1H), 1.70 (m, 1H), 1.39 (s, 27H), 1.29 (d, J=6 Hz, 3H), 1.25 (m, 1H), 0.96 (d, J=7 Hz, 3H), 0.94 (t, J=7 Hz, 3H)
$^{13}C$ NMR (125 MHz, $C_6D_6$, δ/ppm)
77.8, 64.2 (br), 51.0, 35.9, 32.9, 25.7, 23.22, 23.21

EXAMPLE 38

Synthesis of $Nb(NCMe_2CH_2CMe_3)(O^tBu)_3$ 2.10 g of tert-butanol and 2.45 g of 1,1,3,3-tetramethylbutylamine were added to 28.6 mL of a hexane solution (1.65M) of butyllithium in argon atmosphere, followed by stirring at room temperature for 12 hours. This solution was added to a hexane (5 mL) suspension of 4.66 g (9.46 mmol) of niobium pentabromide, followed by stirring at room temperature for 24 hours. Insoluble matters were filtered off, and a solvent was distilled away from the filtrate under reduced pressure. The residue obtained was distilled under reduced pressure to obtain 2.07 g of pale yellow liquid (yield: 50%). This liquid was dissolved in $C_6D_6$, and $^1H$ NMR and $^{13}C$ NMR spectra were measured. As a result, it was confirmed that the material is $Nb(NCMe_2CH_2CMe_3)(O^tBu)_3$.

EXAMPLE 39

Synthesis of (methylimido)tris(1,1-diethylpropyloxo)-tantalum ($Ta(NMe)(OCEt_3)_3$)

2.11 g of 3-ethyl-3-pentanol and 7.5 mL of a tetrahydrofuran solution (2.0M) of methylamine were added to 18.4 mL of a hexane solution (1.65M) of butyllithium in argon atmosphere, and the resulting mixture was stirred at room temperature for 1 hour, followed by drying under reduced pressure. 20 mL of hexane was added to the remaining white solid to prepare slurry. The slurry was added to a hexane (5 mL) suspension of 2.17 g (6.06 mmol) of tantalum pentachloride, followed by stirring at room temperature for 12 hours. Insoluble matters were filtered off, and a solvent was distilled away from the filtrate under reduced pressure. The residue obtained was distilled under reduced pressure to obtain 1.07 g of colorless liquid (yield: 32%). This liquid was cooled to room temperature and allowed to stand for several hours. As a result, a colorless solid was formed.

$^1H$ NMR (500 MHz, $C_6D_6$, δ/ppm)
3.91 (s, 3H), 1.63 (q, J=8 Hz, 18H), 0.95 (t, J=8 Hz, 27H)
$^{13}C$ NMR (125 MHz, $C_6D_6$, δ/ppm)
84.5, 48.0, 32.3, 8.6

EXAMPLE 40

Synthesis of (ethylimido)tris(1,1-diethylpropyloxo) tantalum ($Ta(NEt)(OCEt_3)_3$)

2.75 g of 3-ethyl-3-pentanol and 1.22 g of a toluene solution (70 wt %) of ethylamine were added to 23.9 mL of a hexane solution (1.65M) of butyllithium in argon atmosphere, and the resulting mixture was stirred at room temperature for 10 hours, followed by drying under reduced pressure. 20 mL of hexane was added to the remaining white solid to prepare slurry. The slurry was added to a hexane (5 mL) suspension of 2.83 g (7.90 mmol) of tantalum pentachloride, followed by stirring at room temperature for 12 hours. Insoluble matters were filtered off, and a solvent was distilled away from the filtrate under reduced pressure. The residue obtained was distilled under reduced pressure to obtain 3.02 g of colorless liquid (yield: 67%).

$^1H$ NMR (500 MHz, $C_6D_6$, δ/ppm)
4.09 (q, J=7 Hz, 2H), 1.64 (q, J=8 Hz, 18H), 1.24 (t, J=7 Hz, 3H), 0.94 (t, J=8 Hz, 27H)
$^{13}C$ NMR (125 MHz, $C_6D_6$, δ/ppm)
84.4, 55.5, 32.3, 21.0, 8.7

EXAMPLE 41

Synthesis of (isopropylimido)tris(1,1-diethylpropyloxo)-tantalum ($Ta(N^iPr)(OCEt_3)_3$)

2.49 g of 3-ethyl-3-pentanol and 846 mg of isopropylamine were added to 21.7 mL of a hexane solution (1.65M) of butyllithium in argon atmosphere, followed by stirring at room temperature for 12 hours. This solution was added to a hexane (5 mL) suspension of 2.56 g (7.16 mmol) of tantalum pentachloride, followed by stirring at room temperature for 13 hours. Insoluble matters were filtered off, and a solvent was distilled away from the filtrate under reduced pressure. The residue obtained was distilled under reduced pressure to obtain 2.02 g of colorless liquid (yield: 48%).

$^1H$ NMR (500 MHz, $C_6D_6$, δ/ppm)
4.31 (sept., J=7 Hz, 1H), 1.65 (q, J=8 Hz, 18H), 1.29 (d, J=7 Hz, 6H), 0.95 (t, J=8 Hz, 27H)
$^{13}C$ NMR (125 MHz, $C_6D_6$, δ/ppm)
84.3, 61.0, 32.2, 28.6, 8.7

EXAMPLE 42

Synthesis of $Ta(N^tBu)(O^tBu)_3$ 2.70 g of tert-butanol and 1.77 g of tert-butylamine were added to 36.7 mL of a hexane solution (1.65M) of butyllithium in argon atmosphere, followed by stirring at room temperature for 12 hours. This solution was added to a hexane (10 mL) suspension of 4.34 g (12.1 mmol) of tantalum pentachloride, followed by stirring at room temperature for 8 hours. Insoluble matters were filtered off, and a solvent was distilled away from the filtrate under reduced pressure. The residue obtained was distilled under reduced pressure to obtain 4.48 g of colorless liquid (yield: 78%). This liquid was dissolved in $C_6D_6$, and $^1H$ NMR and $^{13}C$ NMR spectra were measured. As a result, it was confirmed that the material is $Ta(N^tBu)(O^tBu)_3$.

EXAMPLE 43

Synthesis of $Ta(N^tBu)(O^tBu)_3$ 1.82 g of tert-butanol and 1.20 g of tert-butylamine were added to 24.8 mL of a hexane solution (1.65M) of butyllithium in argon atmosphere, followed by stirring at room temperature for 12 hours. This solution was added to a hexane (10 mL) suspension of 4.74 g (8.17 mmol) of tantalum pentabromide, followed by stirring at room temperature for 24 hours. Insoluble matters were filtered off, and a solvent was distilled away from the filtrate under reduced pressure. The residue obtained was distilled under reduced pressure to obtain 1.51 g of colorless liquid (yield: 39%). This liquid was dissolved in $C_6D_6$, and $^1H$ NMR and $^{13}C$ NMR spectra were measured. As a result, it was confirmed that the material is $Ta(N^tBu)(O^tBu)_3$.

EXAMPLE 44

Synthesis of (tert-butylimido) tris(1-ethyl-1-methylpropyl-oxo)tantalum ($Ta(N^tBu)(OCEt_2Me)_3$)

2.73 g of 3-methyl-3-pentanol and 1.30 g of tert-butylamine were added to 27.0 mL of a hexane solution (1.65M) of butyllithium in argon atmosphere, followed by stirring at room temperature for 12 hours. This solution was added to a hexane (10 mL) suspension of 3.19 g (8.90 mmol) of tantalum pentachloride, followed by stirring at room temperature for 24 hours. Insoluble matters were filtered off, and a solvent was distilled away from the filtrate under reduced pressure. The residue obtained was distilled under reduced pressure to obtain 3.49 g of colorless liquid (yield: 71%).

$^1H$ NMR (500 MHz, $C_6D_6$, δ/ppm)

1.69-1.56 (m, 12H), 1.40 (s, 9H), 1.31 (s, 9H), 0.95 (t, J=8 Hz, 18H)
$^{13}$C NMR (125 MHz, C$_6$D$_6$, δ/ppm)
82.1, 64.5, 35.5, 35.1, 27.7, 9.1

EXAMPLE 45

Synthesis of (tert-butylimido)tris(1-methyl-1-propyl-butyl- oxo)tantalum (Ta(N$^t$Bu)(OCMePr$_2$)$_3$)

3.33 g of 4-methyl-4-heptanol and 1.25 g of tert-butylamine were added to 25.8 mL of a hexane solution (1.65M) of butyllithium in argon atmosphere, followed by stirring at room temperature for 12 hours. This solution was added to a hexane (10 mL) suspension of 3.06 g (8.53 mmol) of tantalum pentachloride, followed by stirring at room temperature for 24 hours. Insoluble matters were filtered off, and a solvent was distilled away from the filtrate under reduced pressure. The residue obtained was distilled under reduced pressure to obtain 3.89 g of colorless liquid (yield: 71%).
$^1$H NMR (500 MHz, C$_6$D$_6$, δ/ppm)
1.63-1.58 (m, 12H), 1.47-1.41 (m, 12H), 1.44 (s, 9H), 1.36 (s, 9H), 0.98 (t, J=7 Hz, 18H)
$^{13}$C NMR (125 MHz, C$_6$D$_6$, δ/ppm)
81.8, 64.5, 46.1, 35.3, 28.9, 18.1, 15.2

EXAMPLE 46

Synthesis of Ta(N$^t$Pe)(O$^t$Bu)$_3$ 1.39 g of tert-butanol and 1.09 g of tert-pentylamine were added to 18.9 mL of a hexane solution (1.65M) of butyl-lithium in argon atmosphere, followed by stirring at room temperature for 12 hours. This solution was added to a hexane (5 mL) suspension of 2.24 g (6.25 mmol) of tantalum pentachloride, followed by stirring at room temperature for 24 hours. Insoluble matters were filtered off, and a solvent was distilled away from the filtrate under reduced pressure. The residue obtained was distilled under reduced pressure to obtain 2.04 g of colorless liquid (yield: 67%). This liquid was dissolved in C$_6$D$_6$, and $^1$H NMR and $^{13}$C NMR spectra were measured. As a result, it was confirmed that the material is Ta(N$^t$Pe)(O$^t$Bu)$_3$.

EXAMPLE 47

Synthesis of Ta(NCMe$_2$CH$_2$CMe$_3$)(O$^t$Bu)$_3$ 2.37 g of tert-butanol and 2.76 g of 1,1,3,3-tetramethylbutylamine were added to 32.3 mL of a hexane solution (1.65M) of butyllithium in argon atmosphere, followed by stirring at room temperature for 12 hours. This solution was added to a hexane (5 mL) suspension of 3.82 g (10.7 mmol) of tantalum pentachloride, followed by stirring at room temperature for 24 hours. Insoluble matters were filtered off, and a solvent was distilled away from the filtrate under reduced pressure. The residue obtained was distilled under reduced pressure to obtain 4.07 g of colorless liquid (yield: 72%). This liquid was dissolved in C$_6$D$_6$, and $^1$H NMR and $^{13}$C NMR spectra were measured. As a result, it was confirmed that the material is Ta(NCMe$_2$CH$_2$CMe$_3$)(O$^t$Bu)$_3$.

EXAMPLE 48

Synthesis of (tert-butylimido)tris(1-methyl-1-propyl-butyl-oxo)niobium (Nb(N$^t$Bu)(OCMePr$_2$)$_3$)

2.53 g of 4-methyl-4-heptanol was added to 12.4 mL of a hexane solution (1.57M) of butyllithium in argon atmosphere, and the resulting mixture was stirred at room temperature for 12 hours to prepare a lithium 1-methyl-1-propylbutyl oxide solution. This solution was added to slurry obtained by suspending 2.77 g (6.47 mmol) of Nb(N$^t$Bu)Cl$_3$ (pyridine)$_2$ in 12 mL of toluene, followed by stirring at room temperature for 24 hours. Insoluble matters were filtered off, and a solvent was distilled away from the filtrate under reduced pressure. The residue obtained was distilled under reduced pressure to obtain 2.62 g of colorless liquid (yield: 73%).
$^1$H NMR (500 MHz, C$_6$D$_6$, δ/ppm)
1.61-1.56 (m, 12H), 1.47-1.41 (m, 12H), 1.39 (s, 9H), 1.35 (s, 9H), 0.97 (t, J=8 Hz, 18H)
$^{13}$C NMR (125 MHz, C$_6$D$_6$, δ/ppm)
81.5, 64.8 (br), 46.1, 33.8, 28.9, 18.1, 15.3

REFERENCE EXAMPLE 6

Synthesis of (tert-butylimido)tribromodipyridine niobium (Nb(N$^t$Bu)Br$_3$(pyridine)$_2$)

4.62 g (9.39 mmol) of niobium pentabromide was suspended in a mixed liquid of 50 mL of toluene and 5 mL of diethyl ether in argon atmosphere, and 2.29 g of sodium metasilicate and 1.37 g of tert-butylamine were added in this order. After stirring at room temperature for 10 hours, 7.0 mL of pyridine was added, followed by further stirring for 7 hours. Insoluble matters were filtered off, and a solvent and excess pyridine were distilled away from the filtrate under reduced pressure to obtain 3.48 g (6.19 mmol) of yellow solid. Yield was 66%.
$^1$H NMR (500 MHz, C$_6$D$_6$, δ/ppm)
9.52 (br, 2H), 8.81 (d, J=5 Hz, 2H), 6.85 (br, 1H), 6.60 (m, 1H), 6.58 (br, 2H), 6.19 (t, J=7 Hz, 2H), 1.61 (s, 9H)

EXAMPLE 49

Synthesis of Nb(N$^t$Bu)(O$^t$Bu)$_3$ 1.38 g of tert-butanol was added to 11.2 mL of a hexane solution (1.65M) of butyllithium in argon atmosphere, and the resulting mixture was stirred at room temperature for 1 hour to prepare a lithium tert-butoxide solution. This solution was added to a solution obtained by dissolving 3.48 g (6.19 mmol) of Nb(N$^t$Bu)Br$_3$(pyridine)$_2$ in ml of toluene, followed by stirring at room temperature for 24 hours. Insoluble matters were filtered off, and a solvent was distilled away from the filtrate under reduced pressure. The residue obtained was distilled under reduced pressure to obtain 1.81 g of colorless liquid (yield: 76%). This liquid was dissolved in C$_6$D$_6$, and $^1$H NMR and $^{13}$C NMR spectra were measured. As a result, it was confirmed that the material is Nb(N$^t$Bu)(O$^t$Bu)$_3$.

REFERENCE EXAMPLE 7

Synthesis of (sec-butylimido)trichloro(1,2-dimethoxy-ethane)niobium (Nb(N$^s$Bu)Cl$_3$(dme))

6.04 g (22.4 mmol) of niobium pentachloride was dissolved in a mixed liquid of 50 mL of toluene and 5 mL of diethyl ether in argon atmosphere, and 4.98 g of sec-butylamine, 2.34 mL of 1,2-dimethoxyethane and 7.69 g of zinc (II) chloride were added in this order while cooling with ice bath. After stirring at room temperature for 21 hours, the resulting mixture was allowed to stand at −20° C. for 6 hours while cooling. Insoluble matters were filtered off, and a solvent was distilled away from the filtrate under reduced pressure to obtain 6.73 g (18.7 mmol) of yellow solid. Yield was 83%.

$^1$H NMR (500 MHz, C$_6$D$_6$, δ/ppm)

3.82 (sext, J=7 Hz, 1H), 3.47 (s, 3H), 3.29 (s, 3H), 3.09 (m, 2H), 3.08 (m, 2H), 1.74 (m, 1H), 1.37 (m, 1H), 1.25 (d, J=7 Hz, 3H), 1.14 (t, J=7 Hz, 3H)

$^{13}$C NMR (125 MHz, C$_6$D$_6$, δ/ppm)

75.1, 73.3, 70.4, 68.7, 61.8, 31.7, 20.9, 11.6

EXAMPLE 50

Synthesis of (sec-butylimido)tri(tert-butoxo)niobium (Nb(N$^s$Bu)(O$^t$Bu)$_3$)

4.15 g of tert-butanol was added to 33.9 mL of a hexane solution (1.65M) of butyllithium in argon atmosphere, and the resulting mixture was stirred at room temperature for 1 hour to prepare a lithium tert-butoxide solution. This solution was added to a solution obtained by dissolving 6.73 g (18.7 mmol) of Nb(N$^s$Bu)Cl$_3$(dme) in 10 ml of toluene, followed by stirring at room temperature for 10 hours. Insoluble matters were filtered off, and a solvent was distilled away from the filtrate under reduced pressure. The residue obtained was distilled under reduced pressure to obtain 6.09 g of pale yellow liquid (yield: 85%).

$^1$H NMR (500 MHz, C$_6$D$_6$, δ/ppm)

3.69 (br, 1H), 1.71 (m, 1H), 1.45 (m, 1H), 1.37 (s, 27H), 1.24 (d, J=6 Hz, 3H), 0.98 (t, J=7 Hz, 3H)

$^{13}$C NMR (125 MHz, C$_6$D$_6$, δ/ppm)

77.8, 67.8 (br), 34.0, 32.9, 24.6, 11.8

REFERENCE EXAMPLE 8

Synthesis of (sec-butylimido)trichlorodipyridine tantalum (Ta(N$^s$Bu)Cl$_3$(pyridine)$_2$)

8.75 g (24.4 mmol) of tantalum pentachloride was suspended in a mixed liquid of 70 mL of toluene and 7 mL of diethyl ether in argon atmosphere, and 5.96 g of sodium metasilicate and 3.57 g of sec-butylamine were added in this order. After stirring at room temperature for 20 hours, 20 mL of pyridine was added, followed by further stirring for 5 hours. Insoluble matters were filtered off, and a solvent and excess pyridine were distilled away from the filtrate under reduced pressure to obtain 9.69 g (18.8 mmol) of pale yellow solid. Yield was 77%.

$^1$H NMR (500 MHz, C$_6$D$_6$, δ/ppm)

9.16 (br, 2H), 8.83 (d, J=7 Hz, 2H), 6.86 (br, 1H), 6.73 (t, J=7 Hz, 1H), 6.52 (br, 2H), 6.32 (t, J=7 Hz, 2H), 5.06 (sext, J=6 Hz, 1H), 1.90 (m, 1H), 1.59 (m, 1H), 1.42 (d, J=6 Hz, 3H), 1.28 (t, J=7 Hz, 3H)

$^{13}$C NMR (125 MHz, C$_6$D$_6$, δ/ppm)

153.1, 152.2, 139.6, 138.4, 124.4, 124.2, 68.3, 33.8, 23.5, 11.8

EXAMPLE 51

Synthesis of (sec-butylimido)tri(tert-butoxo)tantalum (Ta(N$^s$Bu)(O$^t$Bu)$_3$)

4.17 g of tert-butanol was added to 34.1 mL of a hexane solution (1.65M) of butyllithium in argon atmosphere, and the resulting mixture was stirred at room temperature for 1 hour to prepare a lithium tert-butoxide solution. This solution was added to a solution obtained by dissolving 9.69 g (18.8 mmol) of Ta(N$^s$Bu)Cl$_3$(pyridine)$_2$ in 10 ml of toluene, followed by stirring at room temperature for 10 hours. Insoluble matters were filtered off, and a solvent was distilled away from the filtrate under reduced pressure. The residue obtained was distilled under reduced pressure to obtain 4.48 g of pale yellow liquid (yield: 51%).

$^1$H NMR (500 MHz, C$_6$D$_6$, δ/ppm)

4.05 (sext, J=6 Hz, 1H), 1.71 (m, 1H), 1.50 (m, 1H), 1.38 (s, 27H), 1.30 (d, J=6 Hz, 3H), 1.06 (t, J=7 Hz, 3H)

$^{13}$C NMR (125 MHz, C$_6$D$_6$, δ/ppm)

78.2, 66.8, 35.4, 32.9, 26.4, 12.0

REFERENCE EXAMPLE 9

Synthesis of (1,1,3,3-tetramethylbutylimido)trichloro-dipyridine niobium (Nb(NCMe$_2$CH$_2$CMe$_3$)Cl$_3$(pyridine)$_2$ 7.63 g (28.2 mmol) of niobium pentachloride was suspended in a mixed liquid of 50 mL of toluene and 5 mL of diethyl ether in argon atmosphere, and 6.89 g of sodium metasilicate and 7.30 g of 1,1,3,3-tetramethylbutylamine were added in this order. After stirring at room temperature for 3 hours, 15.0 mL of pyridine was added, followed by further stirring for 24 hours. Insoluble matters were filtered off, and a solvent and excess pyridine were distilled away from the filtrate under reduced pressure to obtain 10.7 g (22.0 mmol) of dark yellow solid. Yield was 78%.

$^1$H NMR (500 MHz, C$_6$D$_6$, δ/ppm)

9.17 (br, 2H), 8.89 (br, 2H), 6.83 (br, 1H), 6.70 (t, J=8 Hz, 1H), 6.52 (br, 2H), 6.31 (br, 2H), 1.87 (s, 2H), 1.67 (s, 6H), 1.15 (s, 9H)

REFERENCE EXAMPLE 10

Synthesis of tris(dimethylamido)(1,1,3,3-tetramethylbutyl-imido)niobium (Nb(NCMe$_2$CH$_2$CMe$_3$)(NMe$_2$)$_3$)

1.63 g (3.37 mmol) of Nb(NCMe$_2$CH$_2$CMe$_3$)Cl$_3$(pyridine)$_2$ was suspended in 5 mL of toluene in argon atmosphere, and 10.8 g of hexane slurry (5.28 wt %) of lithium dimethylamide was added. After stirring at room temperature for 20 hours, insoluble matters were filtered off, and a solvent was distilled away from the filtrate under reduced pressure. The residue was distilled under reduced pressure to obtain 418 mg (1.18 mmol) of dark yellow liquid. Yield was 35%.

$^1$H NMR (500 MHz, C$_6$D$_6$, δ/ppm)

3.19 (s, 18H), 1.77 (s, 2H), 1.51 (s, 6H), 1.16 (s, 9H)

$^{13}$C NMR (125 MHz, C$_6$D$_6$, δ/ppm)

72.9, 57.9, 47.2, 34.1, 32.3, 32.2

EXAMPLE 52

Synthesis of (1,1,3,3-tetramethylbutylimido)(triisopropoxo)niobium (Nb(NCMe$_2$CH$_2$CMe$_3$)(O$^i$Pr)$_3$ A solution obtained by dissolving 410 mg (1.16 mmol) of Nb (NCMe$_2$CH$_2$CMe$_3$)(NMe$_2$)$_3$ in 4 mL of toluene was cooled to −78° C. in argon atmosphere, and a toluene (4 mL) solution of isopropyl alcohol (210 mg) was added dropwise over 30 minutes. After stirring at room temperature for 4 hours, a solvent was distilled away under reduced pressure. The residue was sublimated under reduced pressure to obtain 310 mg of white solid (yield: 67%).

$^1$H NMR (500 MHz, C$_6$D$_6$, δ/ppm)

5.18 (sept, J=6 Hz, 3H), 1.98 (s, 2H), 1.51 (s, 6H), 1.48 (d, J=6 Hz, 18H), 1.05 (s, 9H)

$^{13}$C NMR (125 MHz, C$_6$D$_6$, δ/ppm)
77.9, 70.5, 59.1, 33.1, 32.2, 26.9, 25.9

EXAMPLE 53

Synthesis of (tert-butylimido)(triisopropoxo)niobium (Nb(N$^t$Bu)(O$^i$Pr)$_3$)

A solution obtained by dissolving 415 mg (1.09 mmol) of Nb(N$^t$Bu)(NEt$_2$)$_3$ in 10 mL of toluene was cooled to −78° C. in argon atmosphere, and a toluene (10 mL) solution of isopropyl alcohol (197 mg) was added dropwise over 30 minutes. After stirring at −78° C. for 3 hours, a solvent was distilled away under reduced pressure. The residue was dissolved in 5 mL of hexane at room temperature, and cooled to −78° C. to obtain 255 mg of white solid (yield: 68%).

$^1$H NMR (500 MHz, C$_6$D$_6$, δ/ppm)
5.12 (m, 3H), 1.45 (d, J=7 Hz, 18H), 1.38 (s, 9H)
$^{13}$C NMR (125 MHz, C$_6$D$_6$, δ/ppm)
77.7, 65.7 (br), 33.8, 26.7

EXAMPLE 54

Synthesis of (tert-butylimido)(triethoxo)niobium

Nb(N$^t$Bu)(OEt)$_3$)

A solution obtained by dissolving 826 mg (2.17 mmol) of Nb(N$^t$Bu)(NEt$_2$)$_3$ in 10 mL of toluene was cooled to −78° C. in argon atmosphere, and a toluene (10 mL) solution of ethanol (300 mg) was added dropwise over 30 minutes. After stirring at −78° C. for 3 hours, a solvent was distilled away under reduced pressure. The residue was dissolved in 5 mL of hexane at room temperature, and the resulting solution was cooled to −78° C. to obtain 255 mg of white solid (yield: 39%).

$^1$H NMR (500 MHz, C$_6$D$_6$, δ/ppm)
4.72 (d, J=7 Hz, 6H), 1.50 (d, J=7 Hz, 9H), 1.33 (s, 9H)
$^{13}$C NMR (125 MHz, C$_6$D$_6$, δ/ppm)
72.1, 66.7 (br), 33.4, 20.0

REFERENCE EXAMPLE 11

Synthesis of tris(diethylamido)(tert-pentylimido) niobium (Nb(N$^t$Pe)(NEt$_2$)$_3$)

4.36 g of diethylamine was added to 36.1 mL of a hexane solution (1.65M) of butyllithium in argon atmosphere, and the resulting mixture was stirred for 12 hours to prepare a lithium diethylamide solution. This solution was added to a toluene (30 mL) suspension of 7.44 g (19.9 mmol) of Nb(N$^t$Pe)Cl$_3$(dme). After stirring at room temperature for 12 hours, insoluble matters were filtered off, and a solvent was distilled away from the filtrate under reduced pressure. The residue was distilled under reduced pressure to obtain 2.70 g (6.85 mmol) of yellowish brown liquid. Yield was 34%.

$^1$H NMR (500 MHz, C$_6$D$_6$, δ/ppm)
3.68 (q, J=7 Hz, 12H), 1.64 (q, J=8 Hz, 2H), 1.37 (s, 6H), 1.15 (t, J=7 Hz, 18H), 1.13 (t, J=8 Hz, 3H)

EXAMPLE 55

Synthesis of (tert-pentylimido)(triisopropoxo)niobium (Nb(N$^t$Pe)(O$^i$Pr)$_3$)

A solution obtained by dissolving 921 mg (2.33 mmol) of Nb(N$^t$Pe)(NEt$_2$)$_3$ in 10 mL of toluene was cooled to −78° C. in argon atmosphere, and a toluene (10 mL) solution of isopropyl alcohol (421 mg) was added dropwise over 30 minutes. After stirring at −78° C. for 3 hours, a solvent was distilled away under reduced pressure. The residue was washed with 1 mL of cyclohexane and then dried under reduced pressure to obtain 555 mg of white solid (yield: 67%).

$^1$H NMR (500 MHz, C$_6$D$_6$, δ/ppm)
5.09 (m, 3H), 1.66 (q, J=7 Hz, 2H), 1.41 (d, J=6 Hz, 18H), 1.31 (s, 6H), 1.01 (t, J=7 Hz, 3H)
$^{13}$C NMR (125 MHz, C$_6$D$_6$, δ/ppm)
77.7, 68.8 (br), 33.7, 30.8, 26.7, 9.8

EXAMPLE 56

Synthesis of (tert-pentylimido)(triethoxo)niobium (Nb(N$^t$Pe)(OEt)$_3$)

A solution obtained by dissolving 889 mg (2.25 mmol) of Nb(N$^t$Pe)(NEt$_2$)$_3$ in 10 mL of toluene was cooled to −78° C. in argon atmosphere, and a toluene (10 mL) solution of ethanol (311 mg) was added dropwise over 30 minutes. After stirring at −78° C. for 3 hours, a solvent was distilled away under reduced pressure. The residue was washed with 1 mL of cyclohexane and then dried under reduced pressure to obtain 701 mg of yellow solid (yield: 99%).

$^1$H NMR (500 MHz, C$_6$D$_6$, δ/ppm)
4.68 (q, J=8 Hz, 6H), 1.60 (d, J=8 Hz, 2H), 1.46 (t, J=8 Hz, 9H), 1.26 (s, 6H), 1.02 (t, J=8 Hz, 3H)
$^{13}$C NMR (125 MHz, C$_6$D$_6$, δ/ppm)
71.9, 69.0 (br), 38.5, 30.6, 20.0, 9.9

COMPARATIVE EXAMPLE 3

Formation of Nb-Containing Thin Film Using Nb(OEt)$_5$

Nb(OEt)$_5$ was used as a raw material, and film formation was conducted on SiO$_2$/Si substrate for 1 hour at raw material temperature of 97° C., carrier gas (Ar) flow rate of 30 sccm, raw material pressure of 50 Torr, diluent gas (Ar) flow rate of 210 sccm, reaction gas (O$_2$) flow rate of 60 sccm, substrate temperature of 400° C. and pressure in reaction chamber of 4 Torr by CVD method using an apparatus shown in FIG. 2. The film prepared was measured with fluorescent X-ray analyzer, and as a result, characteristic X-ray of Nb was detected. Film composition was confirmed with X-ray photoelectron spectroscopy, and as a result, it was niobium oxide. Film thickness was about 14 nm.

COMPARATIVE EXAMPLE 4

Formation of Nb-Containing Thin Film Using Nb(OEt)$_5$

Nb(OEt)$_5$ was used as a raw material, and film formation was conducted on SiO$_2$/Si substrate for 1 hour at raw material temperature of 97° C., carrier gas (Ar) flow rate of 30 sccm, raw material pressure of 50 Torr, diluent gas (Ar) flow rate of 210 sccm, reaction gas (O$_2$) flow rate of 60 sccm, substrate temperature of 200° C. and pressure in reaction chamber of 4 Torr by CVD method using an apparatus shown in FIG. 2. As a result of measurement with fluorescent X-ray analyzer, characteristic X-ray of Nb was not detected.

EXAMPLE 57

Formation of Nb-Containing Thin Film Using Nb(N$^t$Bu)(O$^t$Bu)$_3$

Nb(N$^t$Bu)(O$^t$Bu)$_3$ was used as a raw material, and film formation was conducted on SiO$_2$/Si substrate for 1 hour at raw material temperature of 40° C., carrier gas (Ar) flow rate of 30 sccm, raw material pressure of 50 Torr, diluent gas (Ar) flow rate of 210 sccm, reaction gas ($O_2$) flow rate of 60 sccm, substrate temperature of 400° C. and pressure in reaction chamber of 4 Torr by CVD method using an apparatus shown in FIG. 2. The film prepared was measured with fluorescent X-ray analyzer, and as a result, characteristic X-ray of Nb was detected. Film composition was confirmed with X-ray photoelectron spectroscopy, and as a result, it was niobium oxide. Film thickness was about 210 nm.

EXAMPLE 58

Formation of Nb-Containing Thin Film Using Nb(N$^t$Bu)(O$^t$Bu)$_3$

Nb(N$^t$Bu)(O$^t$Bu)$_3$ was used as a raw material, and film formation was conducted on $SiO_2$/Si substrate for 1 hour at raw material temperature of 40° C., carrier gas (Ar) flow rate of 30 sccm, raw material pressure of 50 Torr, diluent gas (Ar) flow rate of 210 sccm, reaction gas ($O_2$) flow rate of 60 sccm, substrate temperature of 200° C. and pressure in reaction chamber of 4 Torr by CVD method using an apparatus shown in FIG. 2. The film prepared was measured with fluorescent X-ray analyzer, and as a result, characteristic X-ray of Nb was detected. Film composition was confirmed with X-ray photoelectron spectroscopy, and as a result, it was niobium oxide. Film thickness was about 220 nm.

EXAMPLE 59

Formation of Nb-Containing Thin Film Using Nb(N$^i$Pr)(O$^t$Bu)$_3$

Nb(N Pr)(O$^t$Bu)$_3$ was used as a raw material, and film formation was conducted on $SiO_2$/Si substrate for 1 hour at raw material temperature of 40° C., carrier gas (Ar) flow rate of 30 sccm, raw material pressure of 50 Torr, diluent gas (Ar) flow rate of 210 sccm, reaction gas ($O_2$) flow rate of 60 sccm, substrate temperature of 400° C. and pressure in reaction chamber of 4 Torr by CVD method using an apparatus shown in FIG. 2. The film prepared was measured with fluorescent X-ray analyzer, and as a result, characteristic X-ray of Nb was detected. Film composition was confirmed with X-ray photoelectron spectroscopy, and as a result, it was niobium oxide. Film thickness was about 250 nm.

EXAMPLE 60

Formation of Nb-Containing Thin Film Using Nb(N$^i$Pr)(O$^t$Bu)$_3$

Nb(N$^i$Pr)(O$^t$Bu)$_3$ was used as a raw material, and film formation was conducted on $SiO_2$/Si substrate for 1 hour at raw material temperature of 40° C., carrier gas (Ar) flow rate of 30 sccm, raw material pressure of 50 Torr, diluent gas (Ar) flow rate of 210 sccm, reaction gas ($O_2$) flow rate of 60 sccm, substrate temperature of 200° C. and pressure in reaction chamber of 4 Torr by CVD method using an apparatus shown in FIG. 2. The film prepared was measured with fluorescent X-ray analyzer, and as a result, characteristic X-ray of Nb was detected. Film composition was confirmed with X-ray photoelectron spectroscopy, and as a result, it was niobium oxide. Film thickness was about 240 nm.

COMPARATIVE EXAMPLE 5

Formation of Ta-Containing Thin Film Using Ta(OEt)$_5$

Ta(OEt)$_5$ was used as a raw material, and film formation was conducted on $SiO_2$/Si substrate for 1 hour at raw material temperature of 98° C., carrier gas (Ar) flow rate of 30 sccm, raw material pressure of 50 Torr, diluent gas (Ar) flow rate of 210 sccm, reaction gas ($O_2$) flow rate of 60 sccm, substrate temperature of 400° C. and pressure in reaction chamber of 4 Torr by CVD method using an apparatus shown in FIG. 2. The film prepared was measured with fluorescent X-ray analyzer, and as a result, characteristic X-ray of Ta was detected. Film composition was confirmed with X-ray photoelectron spectroscopy, and as a result, it was tantalum oxide. Film thickness was about 30 nm.

COMPARATIVE EXAMPLE 6

Formation of Ta-Containing Thin Film Using Ta(OEt)$_5$

Ta(OEt)$_5$ was used as a raw material, and film formation was conducted on $SiO_2$/Si substrate for 1 hour at raw material temperature of 98° C., carrier gas (Ar) flow rate of 30 sccm, raw material pressure of 50 Torr, diluent gas (Ar) flow rate of 210 sccm, reaction gas ($O_2$) flow rate of 60 sccm, substrate temperature of 200° C. and pressure in reaction chamber of 4 Torr by CVD method using an apparatus shown in FIG. 2. As a result of measurement with fluorescent X-ray analyzer, characteristic X-ray of Ta was not detected.

EXAMPLE 61

Formation of Ta-Containing Thin Film Using Ta(N$^t$Bu)(O$^t$Bu)$_3$

Ta(N$^t$Bu)(O$^t$Bu)$_3$ was used as a raw material, and film formation was conducted on $SiO_2$/Si substrate for 1 hour at raw material temperature of 38° C., carrier gas (Ar) flow rate of 30 sccm, raw material pressure of 50 Torr, diluent gas (Ar) flow rate of 210 sccm, reaction gas ($O_2$) flow rate of 60 sccm, substrate temperature of 400° C. and pressure in reaction chamber of 4 Torr by CVD method using an apparatus shown in FIG. 2. The film prepared was measured with fluorescent X-ray analyzer, and as a result, characteristic X-ray of Ta was detected. Film composition was confirmed with X-ray photoelectron spectroscopy, and as a result, it was tantalum oxide. Film thickness was about 270 nm.

EXAMPLE 62

Formation of Ta-Containing Thin Film Using Ta(N$^t$Bu)(O$^t$Bu)$_3$

Ta(N$^t$Bu)(O$^t$Bu)$_3$ was used as a raw material, and film formation was conducted on $SiO_2$/Si substrate for 1 hour at raw material temperature of 38° C., carrier gas (Ar) flow rate of 30 sccm, raw material pressure of 50 Torr, diluent gas (Ar) flow rate of 210 sccm, reaction gas ($O_2$) flow rate of 60 sccm, substrate temperature of 200° C. and pressure in reaction chamber of 4 Torr by CVD method using an apparatus shown in FIG. 2. The film prepared was measured with fluorescent X-ray analyzer, and as a result, characteristic X-ray of Ta was detected. Film composition was confirmed with X-ray photoelectron spectroscopy, and as a result, it was tantalum oxide. Film thickness was about 100 nm.

EXAMPLE 63

Formation of Ta-Containing Thin Film Using Ta(N$^i$Pr)(O$^t$Bu)$_3$

Ta(N$^i$Pr)(O$^t$Bu)$_3$ was used as a raw material, and film formation was conducted on $SiO_2$/Si substrate for 1 hour at raw material temperature of 40° C., carrier gas (Ar) flow rate of 30 sccm, raw material pressure of 50 Torr, diluent gas (Ar) flow rate of 210 sccm, reaction gas ($O_2$) flow rate of 60 sccm, substrate temperature of 400° C. and pressure in reaction chamber of 4 Torr by CVD method using an apparatus shown in FIG. 2. The film prepared was measured with fluorescent X-ray analyzer, and as a result, characteristic X-ray of Ta was detected. Film composition was confirmed with X-ray photoelectron spectroscopy, and as a result, it was tantalum oxide. Film thickness was about 340 nm.

EXAMPLE 64

Formation of Ta-Containing Thin Film Using Ta(N$^i$Pr)(O$^t$Bu)$_3$

Ta(N$^i$Pr)(O$^t$Bu)$_3$ was used as a raw material, and film formation was conducted on SiO$_2$/Si substrate for 1 hour at raw material temperature of 40° C., carrier gas (Ar) flow rate of 30 sccm, raw material pressure of 50 Torr, diluent gas (Ar) flow rate of 210 sccm, reaction gas (O$_2$) flow rate of 60 sccm, substrate temperature of 200° C. and pressure in reaction chamber of 4 Torr by CVD method using an apparatus shown in FIG. 2. The film prepared was measured with fluorescent X-ray analyzer, and as a result, characteristic X-ray of Ta was detected. Film composition was confirmed with X-ray photoelectron spectroscopy, and as a result, it was tantalum oxide. Film thickness was about 120 nm.

While the invention has been described in detail and with reference to specific embodiments thereof, it is apparent to one skilled in the art that various changes and modifications can be made therein without departing from the spirit and scope thereof.

This application is based on Japanese Patent Application (Application No. 2006-231081) filed Aug. 28, 2006, Japanese Patent Application (Application No. 2007-79924) filed Mar. 26, 2007 and Japanese Patent Application (Application No. 2007-186071) filed Jul. 17, 2007, the entire contents thereof being hereby incorporated by reference.

INDUSTRIAL APPLICABILITY

The imide complex (1) of the present invention has good vapor pressure, and using this as a raw material, it is possible to produce a niobium- or tantalum-containing thin film by a method such as CVD method, ALD method or the like. Industrial value of the present invention is remarkable.

The invention claimed is:

1. An imide complex represented by the general formula (1):

[Chem. 1]

$$M^1(NR^1)(OR^2)_3 \qquad (1)$$

(wherein M$^1$ represents niobium atom or tantalum atom, R$^1$ represents an alkyl group having from 1 to 12 carbon atoms, and R$^2$ represents an alkyl group having from 2 to 13 carbon atoms).

2. The imide complex as claimed in claim 1, wherein R$^1$ represents an alkyl group having from 1 to 10 carbon atoms, and R$^2$ represents isopropyl group or tert-butyl group.

3. The imide complex as claimed in claim 1 or 2, wherein M$^1$ is niobium atom, R$^1$ is propyl group, isopropyl group or tert-butyl group, and R$^2$ is tert-butyl group.

4. The imide complex as claimed in claim 1 or 2, wherein M$^1$ is tantalum atom, R$^1$ is isopropyl group or tert-butyl group, and R$^2$ is tert-butyl group.

5. A method for producing an imide complex represented by the general formula (1):

[Chem. 4]

$$M^1(NR^1)(OR^2)_3 \qquad (1)$$

(wherein M$^1$, R$^1$ and R$^2$ are the same as defined below), which comprises reacting a compound represented by the general formula (2):

[Chem. 2]

$$M^1(NR^1)X_3(L)_r \qquad (2)$$

(wherein M$^1$ represents niobium atom or tantalum atom, R$^1$ represents an alkyl group having from 1 to 12 carbon atoms, X represents halogen atom, L represents 1,2-dimethoxyethane ligand or pyridine ligand, r is 1 when L is 1,2-dimethoxyethane ligand, and r is 2 when L is pyridine ligand), and an alkali metal alkoxide represented by the general formula (3):

[Chem. 3]

$$R^2OM^2 \qquad (3)$$

(wherein R$^2$ represents an alkyl group having from 2 to 13 carbon atoms, and M$^2$ represents an alkali metal).

6. The production method as claimed in claim 5, wherein X is chlorine atom, and M$^2$ is lithium atom, sodium atom or potassium atom.

7. A method for producing an imide complex represented by the general formula (1):

[Chem. 7]

$$M^1(NR^1)(OR^2)_3 \qquad (1)$$

(wherein M$^1$, R$^1$ and R$^2$ are the same as defined below) which comprises reacting a compound represented by the general formula (4):

[Chem. 5]

$$M^1(NR^1)(NR^3R^4)_3 \qquad (4)$$

(wherein M$^1$ represents niobium atom or tantalum atom, R$^1$ represents an alkyl group having from 1 to 12 carbon atoms, and R$^3$ and R$^4$ each independently represent methyl group or ethyl group), and an alcohol represented by the general formula (5):

[Chem. 6]

$$R^2OH \qquad (5)$$

(wherein R$^2$ is an alkyl group having from 2 to 13 carbon atoms).

8. The production method as claimed in claim 7, which comprises using a compound represented by general formula (4) obtained by reacting a compound represented by the formula (2):

[Chem. 8]

$$M^1(NR^1)X_3(L)_r \qquad (2)$$

(wherein M$^1$ represents niobium atom or tantalum atom, R$^1$ represents an alkyl group having from 1 to 12 carbon atoms, X represents halogen atom, L represents 1,2-dimethoxyethane ligand or pyridine ligand, r is 1 when L is 1,2-dimethoxyethane ligand, and r is 2 when L is pyridine ligand), and a compound represented by the general formula (6):

[Chem. 9]

$$LiNR^3R^4 \qquad (6)$$

(wherein $R^3$ and $R^4$ each independently represent methyl group or ethyl group).

9. The production method as claimed in claim 8, wherein X is chlorine atom, and $R^3$ and $R^4$ are simultaneously methyl group or ethyl group.

10. A method for producing an imide complex represented by the general formula (1):

[Chem. 12]

$$M^1(NR^1)(OR^2)_3 \quad (1)$$

(wherein $M^1$, $R^1$ and $R^2$ are the same as defined below), which comprises reacting a compound represented by the general formula (1a):

[Chem. 10]

$$M^1(NR^{1a})(OR^2)_3 \quad (1a)$$

(wherein $M^1$ represents niobium atom or tantalum atom, $R^{1a}$ represents tert-butyl group or isopropyl group, and $R^2$ represents an alkyl group having from 2 to 13 carbon atoms), and an amine represented by the general formula (7):

[Chem. 11]

$$R^1NH_2 \quad (7)$$

(wherein $R^1$ represents an alkyl group having from 1 to 12 carbon atoms, provided that $R^1$ and $R^{1a}$ are not simultaneously the same group).

11. A method for producing an imide complex represented by the general formula (1):

[Chem. 16]

$$M^1(NR^1)(OR^2)_3 \quad (1)$$

(wherein $M^1$, $R^1$ and $R^2$ are the same as defined below), which comprises reacting a metal halide represented by the general formula (8):

[Chem. 13]

$$M^1Y_5 \quad (8)$$

(wherein $M^1$ represents niobium atom or a tantalum atom, and Y represents halogen atom),
an alkali metal alkoxide represented by the general formula (3):

[Chem. 14]

$$R^2OM^2 \quad (3)$$

(wherein $R^2$ represents an alkyl group having from 2 to 13 carbon atoms, and $M^2$ represents an alkali metal), and lithium amide represented by the general formula (9):

[Chem. 15]

$$R^1NHLi \quad (9)$$

(wherein $R^1$ represents an alkyl group having from 1 to 12 carbon atoms).

12. The production method as claimed in claim 11, wherein Y is chlorine atom, and $M^2$ is lithium atom, sodium atom or potassium atom.

13. A method for producing a niobium- or tantalum-containing thin film, which comprises using an imide complex represented by the general formula (1):

[Chem. 17]

$$M^1(NR^1)(OR^2)_3 \quad (1)$$

(wherein $M^1$ represents niobium atom or tantalum atom, $R^1$ represents an alkyl group having from 1 to 12 carbon atoms, and $R^2$ represents an alkyl group having from 2 to 13 carbon atoms).

14. A niobium- or tantalum-containing thin film produced by the method as claimed in claim 13.

* * * * *